(12) United States Patent
Nahas et al.

(10) Patent No.: US 11,078,461 B2
(45) Date of Patent: Aug. 3, 2021

(54) COMPOSITIONS AND METHODS FOR IMPLANTATION OF PROCESSED ADIPOSE TISSUE AND PROCESSED ADIPOSE TISSUE PRODUCTS

(71) Applicant: THE JOHNS HOPKINS UNIVERSITY, Baltimore, MD (US)

(72) Inventors: Zayna Nahas, Palo Alto, CA (US); Jennifer H. Elisseeff, Baltimore, MD (US); Iwen Wu, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 300 days.

(21) Appl. No.: 15/796,089

(22) Filed: Oct. 27, 2017

(65) Prior Publication Data

US 2018/0127719 A1    May 10, 2018

Related U.S. Application Data

(63) Continuation of application No. 13/383,850, filed as application No. PCT/US2010/045177 on Aug. 11, 2010, now abandoned.

(60) Provisional application No. 61/232,915, filed on Aug. 11, 2009.

(51) Int. Cl.
```
A61K 35/35      (2015.01)
A61K 45/06      (2006.01)
A61K 31/00      (2006.01)
C12N 5/077      (2010.01)
A61L 27/36      (2006.01)
```
(52) U.S. Cl.
CPC ............ *C12N 5/0653* (2013.01); *A61K 31/00* (2013.01); *A61K 35/35* (2013.01); *A61K 45/06* (2013.01); *A61L 27/3633* (2013.01); *A61L 2430/34* (2013.01); *A61L 2430/40* (2013.01); *C12N 2533/90* (2013.01)

(58) Field of Classification Search
None
See application file for complete search history.

(56) References Cited

U.S. PATENT DOCUMENTS

| | | | | |
|---|---|---|---|---|
| 2002/0076400 A1* | 6/2002 | Katz | .................... | C12N 5/0068 424/93.21 |
| 2005/0118228 A1* | 6/2005 | Trieu | .................... | C12N 5/0667 424/423 |
| 2005/0147642 A1 | 7/2005 | Laredo et al. | | |
| 2005/0209705 A1 | 9/2005 | Niederauer et al. | | |
| 2006/0159664 A1* | 7/2006 | Pandit | .................... | A61L 27/3683 424/93.7 |
| 2008/0286268 A1* | 11/2008 | Johnson | .............. | A61L 27/3695 424/130.1 |

FOREIGN PATENT DOCUMENTS

| | | | |
|---|---|---|---|
| WO | 00/53795 A1 | 9/2000 | |
| WO | 2005009497 A1 | 2/2005 | |
| WO | 2006/062989 A1 | 6/2006 | |
| WO | WO 2007/037572 A1 | 4/2007 | |
| WO | WO-2008143402 A1 * | 11/2008 | ......... A61L 27/3604 |
| WO | WO 2009/102452 A2 | 8/2009 | |
| WO | 2008143402 A1 | 7/2010 | |

OTHER PUBLICATIONS

Choi et al. (Journal of Controlled Release, vol. 139, pp. 2-7; electronically available May 28, 2009) (Year: 2009).*
Choi et al. (Journal of Biomedical Material Research A, vol. 97A, No. 3, pp. 292-299; electronically available Mar. 29, 2011) (Year: 2011).*
Kaufman, M., et al., "Autologous Fat Transfer National Consensus Survey: Trends in Techniques for Harvest, Preparation, and Application, and Perception of Short- and Long-Term Results", Plastic and Reconstructive Surgery. vol. 119(1), Jan. 2007, pp. 323-331.
Uriel, S., et al., "The Role of Adipose Derived Protein Hydrogels in Adipogenesis", Biomaterials. vol. 29, 2008, pp. 3712-3719.
Creemers, L., et al., "Microassay for the assessment of low levels of hydroxyproline", Biotechniques. vol. 22(4), 1997, pp. 656-658.
Woessner, J., "The determination of hydroxyproline in tissue and protein samples containing small proportions of this imino acid", Arch Biochem Biophys. vol. 93, 1961, pp. 440-4477.
Liang, H., et al., "The effects of crosslinking degree of an acellular biological tissue on its tissue regeneration pattern" Biomaterials. 25:3541-3552, 2004.
Kelly, J., et al., "Contact with existing adipose tissue is inductive for adipogenesis in matrigel", Tissue Eng. Jul. 2006;12(7):2041-7.
Stillaert, F., et al., "Host rather than graft origin of Matrigel-induced adipose tissue in the murine tissue-engineering chamber", Tissue Eng. Sep. 2007;13(9):2291-300.
Chaubey, A., et al., "Extracellular Matrix Components as Modulators of Adult Stem Cell Differentiation in an Adipose System", Journal of Bioactive and Compatible Polymers. Burg 2008; 23; 20.
Patent Examination Report for related AU 2010 282571 (2014).
Search Report for related CN 201080045640.4 (2012).

(Continued)

*Primary Examiner* — Soren Harward
*Assistant Examiner* — Paul D. Pyla
(74) *Attorney, Agent, or Firm* — Casimir Jones, S.C.; Lisa V. Mueller

(57) ABSTRACT

The invention provides compositions and methods for the preparation of processed adipose tissue. The invention further provides methods of use of the processed adipose tissue.

36 Claims, 16 Drawing Sheets

(56) References Cited

OTHER PUBLICATIONS

Search Report for related EP 10808697.6 (2013).
Search Report for related CA 2,770,490 (2018).
Search Report and Written Opinion for related PCT/US2010/045177 (2011).

* cited by examiner

FIG. 12A
Control
FIG. 12B
5mM EDC
FIG. 12C
1% HMDC Tween-20
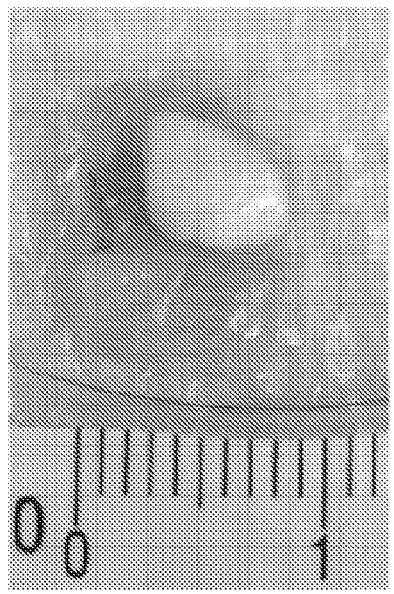
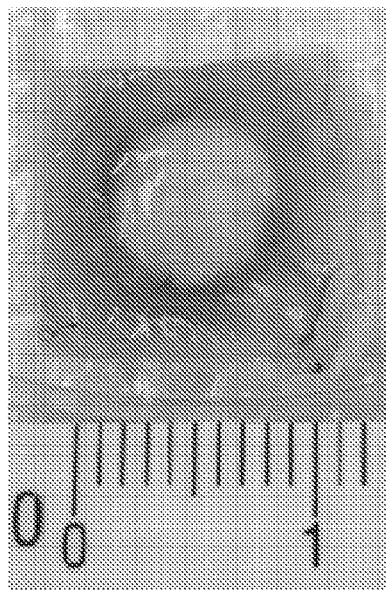
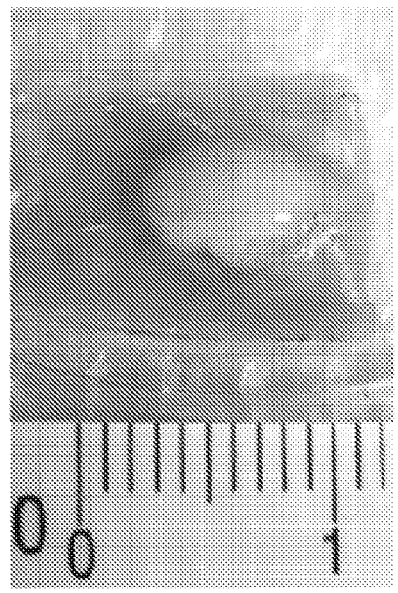

COMPOSITIONS AND METHODS FOR IMPLANTATION OF PROCESSED ADIPOSE TISSUE AND PROCESSED ADIPOSE TISSUE PRODUCTS

CROSS REFERENCE TO RELATED APPLICATIONS

This application is a Continuation of U.S. patent application Ser. No. 13/383,850, filed Mar. 30, 2012, which is a 35 U.S.C. § 371 U.S. national entry of International Application PCT/US2010/045177, having an international filing date of Aug. 11, 2010, which claims priority to U.S. Provisional Application 61/232,915, filed Aug. 11, 2009.

BACKGROUND

The field of regenerative medicine aims to provide tissue substitutes for reconstruction secondary to trauma, disease or congenital abnormalities. While biomaterials and cells are often employed to regenerate new tissues, these methods tend to be costly and require significant time for new tissue formation. Restoration of soft tissue form is critical for a number of applications including trauma reconstruction, breast reconstruction, and cosmetics (nasolabial folds, wrinkles, etc). In general there are two approaches today; 1.) injection/transfer of biological tissue (fat) or 2.) injection or implantation of a synthetic or naturally derived material. In both cases, the transplanted tissue or biomaterial will eventually be degraded and replacement is required.

Reconstruction using patient tissue can provide permanent restoration of tissue in some situations. However, such procedures also have their limitations. Breast reconstruction after mastectomy can include the use of tissue flaps of muscle and adipose tissue either from the abdomen or back which are pulled over to the reconstruction site. Such flaps are necessarily limited in size by the amount of tissue present in the woman for use, and transfer of muscle from the abdomen or back can extend recovery time and result in donor site morbidity. The persistence of fat transfer varies widely with reports of anywhere between 30-90%. Persistence is also often surgeon and technique dependent. Such loss of persistence requires multiple procedures to maintain the desired correction. The donor site morbidity associated with autologous fat transfer is also a significant concern. In addition, implanted adipose tissue often leads to post-operative calcifications. This phenomena is of particular importance for women with a history of breast cancer undergoing breast reconstruction following mastectomy, as the calcifications may interfere with mammography readings and result in multiple, unnecessary breast biopsies and anxiety. Finally, for many patients undergoing chemotherapy and radiation for cancer, the associated cachexia leaves them without the adipose volume they would require for autologous fat transfer.

SUMMARY OF THE INVENTION

The invention provides processed adipose tissue compositions and methods for their preparation and use.

The invention provides compositions including processed adipose tissue having a decellularized adipose tissue extracellular matrix to which viable cells securely attach.

The processed adipose tissue of the invention may include one or more materials at least one (e.g. 1, 2, 3, 4, 5, 6, 7, 8, 9, 10, 11, or 12) material from the group consisting of anesthetic, analgesic, antibiotic, antimicrobial, growth factors, cryopreservative, antioxidant, free radical scavenger, caspase inhibitor, vitamin, lipoaspirate, and a cell.

In certain embodiments, the decellularized adipose includes cross-linking agent. Crosslinking agents include, but are not limited to, carbodiimide (EDC), hexamethylene diisocyanate (HMDC), gluteraldehyde, proanthocyanidin, ribose, threose, and lysyl oxidase, carbodiimide, polyepoxy ethers, divinyl sulfone (DVS), genipin, polyaldehyde and diphenylphosphoryl azide (DPPA), genipin, epoxy compounds, dialdehyde starch, glutaraldehyde, formaldehyde, dimethyl suberimidate, carbodiimides, succinimidyls, diisocyanates, and acyl azide; or any combination thereof.

In certain embodiments, the processed adipose tissue further includes a biopolymer scaffold. In certain embodiments, the processed adipose tissue and biopolymer scaffold further include a biopolymer cross-linking agent. In certain embodiments, the processed adipose tissue includes a polymerization initiator.

Biopolymer scaffolds include, but are not limited to, hyaluronic acid, PEG-DA, chondroitin sulfate, partially or fully hydrolyzed poly(vinyl alcohol), poly(vinylpyrrolidone), poly(ethyloxazoline), poly(ethylene oxide)-co-polypropylene oxide) block copolymers (poloxamers and meroxapols), poloxamines, carboxymethyl cellulose, and hydroxyalkylated celluloses such as hydroxyethyl cellulose and methylhydroxypropyl cellulose, polypeptides, polysaccharides or carbohydrates, Ficoll® polysucrose, dextran, heparan sulfate, heparin, alginate, gelatin, collagen, albumin, ovalbumin, and copolymers or blends thereof.

Polymerization initiators include, but are not limited to, eosin Y, 1-vinyl 2-pyrrolidone NVP, and triethanolamine; and Irgacure D2959.

In certain embodiments, the processed adipose tissue is essentially free of a basement membrane. In certain embodiments, the processed adipose tissue includes (i.e., is not essentially free of) a basement membrane.

The processed adipose tissue of the invention is preferably substantially non-immunogenic when implanted in a subject.

The processed adipose tissue of the invention preferably contains 0.2 µg/mg or less (i.e., undetectable level of DNA to 0.2 µg of DNA), 0.1 µs/mg or less, 0.05 µg/mg or less, 0.025 µg/mg or less, 0.1 µg/mg or less, or 0.005 µg/mg or less of DNA.

The processed adipose tissue of the invention preferably contains 10% or less (i.e., undetectable level of lipid to 10% lipid), 5% or less, 2% or less, 1% or less, 0.5% or less, 0.25% or less, 0.1% or less, 0.05% or less, 0.01% or less, 0.001% or less lipid (w/w).

The processed adipose tissue of the invention preferably has a complex viscosity (η) of $10^4$-$10^5$ Pas; $1\times10^4$-$3\times10^5$ Pas; $2\times10^4$-$2\times10^5$ Pas; $3\times10^4$-$1\times10^5$ Pas; $1\times10^4$-$8\times10^5$ Pas; or $1\times10^4$-$9\times10^5$ Pas; or any combination of those ranges.

The processed adipose tissue of the invention preferably has a complex modulus (G*) of $10^3$-$10^5$ Pa; $5\times10^3$-$1\times10^5$ Pa; $1\times10^4$-$1\times10^5$ Pa; $8\times10^3$-$6\times10^4$ Pa; $2\times10^4$-$5\times10^4$ Pa; or $1\times10^4$-$9\times10^4$ Pa; or any combination of those ranges.

The processed adipose tissue of the invention preferably has an elastic modulus (G') of $10^3$-$10^5$ Pa; $5\times10^3$-$1\times10^5$ Pa; $1\times10^4$-$1\times10^5$ Pa; $8\times10^3$-$6\times10^4$ Pa; $2\times10^4$-$5\times10^4$ Pa; or $1\times10^4$-$9\times10^4$ Pa; or any combination of those ranges.

The processed adipose tissue of the invention preferably has a viscous modulus (G") of $10^3$-$10^5$ Pa; $5\times10^3$-$1\times10^5$ Pa; $1\times10^4$-$1\times10^5$ Pa; $8\times10^3$-$6\times10^4$ Pa; $2\times10^4$-$5\times10^4$ Pa; or $1\times10^4$-$9\times10^4$ Pa; or any combination of those ranges.

The processed adipose tissue of the invention preferably has a tan (δ) of 0.1-0.2; 0.1-0.5; 0.1-1.0; 0.1-0.3; 0.1-0.4; 0.1-0.75; 0.05-0.5; or 0.05-2.0; or any combination of those ranges.

The processed adipose tissue of the invention preferably contains 50% or more, 60% or more, 70% or more, 80% or more or 90% or more (or any range bracketed by those values) of collagens present in the composition are selected from the group consisting of type I collagen, type II collagen, type III collagen, type IV collagen, type V collagen, type XII collagen.

The processed adipose tissue of the invention preferably contains 50% or more, 60% or more, 70% or more, 80% or more or 90% or more (or any range bracketed by those values) of glycosaminoglycans (GAGs) present in the composition are selected from the group consisting of hyaluronic acid, chondroitin sulfate, dermatan sulfate, keratan sulfate, heparin sulfate.

The processed adipose tissue of the invention preferably is insoluble in water.

The processed adipose tissue of the invention preferably can be prepared using any of the methods provided in the instant application.

In certain embodiments, the adipose tissue is human adipose tissue. In certain embodiments, the adipose tissue is porcine adipose tissue. In certain embodiments, the adipose tissue from a live donor. In certain embodiments, the adipose tissue is from a cadaver donor The invention provides methods for preparation of processed adipose tissue (PAT), particularly processed human adipose tissue (PhAT), including sequentially providing mammalian tissue comprising solid adipose tissue; isolating the adipose from the non-adipose material in the tissue; and decellularizing the adipose or extracting lipid from the adipose or both. The method for decellularizing the adipose or extracting lipid from the adipose include homogenizing or mincing the tissue and manipulating the adipose with a buffer to promote lipid and cell removal to prepare processed adipose tissue. Such the buffers include phosphate buffered saline (PBS). Agents to promote decellularization can include one or more of a weak acid, such as a weak organic acid, a non-ionic detergent, and a bile acid. After treatment of the adipose with a buffer or agent not at or about physiological pH, a buffer to adjust pH of the adipose to physiological pH. The invention provides methods for decellularizing the adipose or extracting lipid from the adipose including contacting the adipose with supercritical $CO_2$. Methods of the invention also include nuclease treatment of the material to remove nucleic acids.

The source of the adipose tissue is mammalian adipose tissue. The mammalian adipose tissue can be obtained from any mammal, most conveniently from larger mammals to provide sufficient starting material. In preferred embodiments, the adipose tissue is human adipose tissue or porcine adipose tissue, from either a live or a cadaver donor.

In certain embodiments, the processed adipose tissue is further formed into particles. In certain embodiments, the decellularized/lipid extracted adipose tissue is further contacted a cross-linking agent, to cross-link, for example, the proteins, such as the collagens, present in the processed adipose tissue. Cross-linking agents for use in such methods include, but are not limited to, carbodiimide (EDC), hexamethylene diisocyanate (HMDC), gluteraldehyde, proanthocyanidin, ribose, threose, and lysyl oxidase, polyepoxy ethers, divinyl sulfone (DVS), genipin, polyaldehyde and diphenylphosphoryl azide (DPPA), genipin, epoxy compounds, dialdehyde starch, glutaraldehyde, formaldehyde, dimethyl suberimidate, carbodiimides, succinimidyls, diisocyanates, and acyl azide; or any combination thereof. The specific ratio of cross-linker to the decellularized/lipid extracted adipose tissue will depend, for example on the specific cross-linker used and the final use of the processed adipose tissue. The amount of cross-linker to be used is determined based on the desired physical properties of the processed adipose tissue that can be determined using standard biophysical or biochemical assay methods.

In certain embodiments, the decellularized/lipid extracted adipose tissue is further combined with a biopolymer scaffold. In certain embodiments, the decellularized/lipid extracted adipose tissue and biopolymer scaffold and further combined with a biopolymer cross-linking agent, the mixture of which can be further contacted with a polymerization agent, and further optionally a polymerization initiator.

Biocompatible polymers for use in with the decellularized/lipid extracted adipose tissue include, but are not limited to, hyaluronic acid, PEG-DA, chondroitin sulfate, partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, polypeptides, polysaccharides or carbohydrates, Ficoll® polysucrose, dextran, heparan sulfate, heparin, alginate, gelatin, collagen, albumin, ovalbumin, and copolymers or blends thereof.

Polymerization initiators for use in with the decellularized/lipid extracted adipose tissue include, but are not limited to, wherein the polymerization initiator comprises an agent selected from the group consisting of eosin Y, 1-vinyl 2-pyrrolidone NVP, and triethanolamine; and Irgacure D2959. In certain embodiments the polymerization initiator includes light.

Methods for preparation of the processed adipose tissue of provided herein can include contacting the adipose with a nuclease, either a non-specific or site specific DNase and/or RNase. In certain embodiments, the adipose tissue is contacted with the nuclease after decellularization and/or lipid extraction.

In certain embodiments, the methods for preparation of the processed adipose tissue can include contacting the adipose with a protease inhibitor at one or more steps of the methods. In a preferred embodiment, the protease inhibitors are biocompatible, or the protease inhibitors are substantially removed or inactivated during the processing such that the final processed adipose tissue is biocompatible.

The method optionally includes sterilizing the processed adipose tissue, for example by irradiation or contact with an appropriate gas.

In certain embodiments, the processed adipose tissue is combined with other agents including, but not limited to anesthetic, antibiotic, growth factors, cryopreservative, antioxidant, free radical scavenger, caspase inhibitor, vitamin, lipoaspirate, and a cell. In certain embodiments, the additional agents are added prior to storage of the processed adipose tissue. In certain embodiments, the additional agents are added after storage, closer to the time of use of the processed adipose tissue by the end user.

In certain embodiments, the processed adipose tissue is essentially free of a basement membrane. Although adipose tissue includes vasculature, and thereby includes basement membranes, certain processing methods of the invention serve to remove vasculature and thereby remove basement membranes. In certain embodiments, the processed adipose tissue does not define a space or partition a space in the manner of a basement membrane, e.g., provide a cell impervious barrier.

In certain embodiments of the invention, the processed adipose tissue includes a basement membrane. In certain embodiments of the invention, the processed adipose tissue includes vasculature, or remnants of vasculature, from the original tissue.

The invention provides composition made by any of the methods of the invention. The compositions provided by the invention can be formulated into pharmaceutical compositions, for example injectable or otherwise implantable pharmaceutical compositions.

The invention further provides kits for making any of the compositions of the invention. The invention also provides kits containing any of the compositions of the invention for use as a biofiller in a subject. Kits can include instructions for use of the kit.

Composition provided by the invention can further comprises one or more materials in the decellularized/lipid extracted adipose tissue including, but not limited to, anesthetic, analgesic, antibiotic, antimicrobial, growth factors, cryopreservative, antioxidant, free radical scavenger, caspase inhibitor, vitamin, lipoaspirate, and a cell.

Certain compositions of the invention further include a cross-linking agent, for example to provide cross-links between the protein molecules, such as the collagen molecules of the decellularized/lipid extracted adipose tissue. Such cross-linking agents include, but are not limited to, carbodiimide (EDC), hexamethylene diisocyanate (HMDC), gluteraldehyde, proanthocyanidin, ribose, threose, and lysyl oxidase, carbodiimide, polyepoxy ethers, divinyl sulfone (DVS), genipin, polyaldehyde and diphenylphosphoryl azide (DPPA), genipin, epoxy compounds, dialdehyde starch, glutaraldehyde, formaldehyde, dimethyl suberimidate, carbodiimides, succinimidyls, diisocyanates, and acyl azide; or any combination thereof.

Certain compositions of the invention further include a biopolymer scaffold, optionally further with one or more of a biopolymer cross-linking agent, a polymerization agent, and a polymerization initiator.

Examples of biopolymer scaffolds include, but are not limited to, hyaluronic acid, PEG-DA, chondroitin sulfate, partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, polypeptides, polysaccharides or carbohydrates, Ficoll® polysucrose, dextran, heparan sulfate, heparin, alginate, gelatin, collagen, albumin, ovalbumin, and copolymers or blends thereof. Examples of polymerization initiators include, but are not limited to, eosin Y, 1-vinyl 2-pyrrolidone NVP, and triethanolamine; and Irgacure D2959.

In certain embodiments, the processed adipose tissue does not define or partition a space.

The compositions provided by the invention have one or more properties that make them useful as biofillers. For example, the processed adipose tissue is a decellularized lipid to which viable cells securely attach and can proliferate. In preferred embodiments, the composition is substantially non-immunogenic when implanted in a subject. In certain embodiments, the composition is essentially free of DNA, such that the processed adipose tissue has 0.2 µg/mg or less, 0.2 µg/mg or less, 0.1 µg/mg or less, 0.05 µg/mg or less, 0.025 µg/mg or less, 0.1 µg/mg or less, or 0.005 µg/mg or less of DNA. In certain embodiments, the composition is essentially free of lipid, such that the processed adipose tissue has 10% or less, 5% or less, 2% or less, 1% or less, 0.5% or less, 0.25% or less, 0.1% or less, 0.05% or less, 0.01% or less, 0.001% or less lipid (w/w).

The biophysical properties of the compositions of the invention can be determined by any known method. In certain embodiments, the processed adipose tissue has a complex viscosity (11) of $10^4$-$10^5$ Pas; $1\times10^4$-$3\times10^5$ Pas; $2\times10^4$-$2\times10^5$ Pas; $3\times10^4$-$1\times10^5$ Pas; $1\times10^4$-$8\times10^5$ Pas; or $1\times10^4$-$9\times10^5$ Pas; or any combination of those ranges. In certain embodiments, the processed adipose tissue has a complex modulus (G*) of $10^3$-$10^5$ Pa; $5\times10^3$-$1\times10^5$ Pa; $1\times10^4$-$1\times10^5$ Pa; $8\times10^3$-$6\times10^4$ Pa; $2\times10^4$-$5\times10^4$ Pa; or $1\times10^4$-$9\times10^4$ Pa; or any combination of those ranges. In certain embodiments, the processed adipose tissue has an elastic modulus (G') of $10^3$-$10^5$ Pa; $5\times10^3$-$1\times10^5$ Pa; $1\times10^4$-$1\times10^5$ Pa; $8\times10^3$-$6\times10^4$ Pa; $2\times10^4$-$5\times10^4$ Pa; or $1\times10^4$-$9\times10^4$ Pa; or any combination of those ranges. In certain embodiments, the processed adipose tissue has a viscous modulus (G") of $10^3$-$10^5$ Pa; $5\times10^3$-$1\times10^5$ Pa; $1\times10^4$-$1\times10^5$ Pa; $8\times10^3$-$6\times10^4$ Pa; $2\times10^4$-$5\times10^4$ Pa; or $1\times10^4$-$9\times10^4$ Pa; or any combination of those ranges. In certain embodiments, the processed adipose tissue has a tan ($\delta$) of 0.1-0.2; 0.1-0.5; 0.1-1.0; 0.1-0.3; 0.1-0.4; 0.1-0.75; 0.05-0.5; or 0.05-2.0; or any combination of those ranges.

The processed adipose tissue provided by the invention preferably include 50% or more, 60% or more, 70% or more, 80% or more or 90% or more of collagens present in the composition are selected from the types present in adipose. Type of collagen include type I collagen, type II collagen, type IV collagen, type V collagen, type XII collagen.

The processed adipose tissue provided by the invention preferably include 60% or more, 70% or more, 80% or more or 90% or more of glycosaminoglycans (GAGs) present in the composition are selected from the types present in adipose tissue. Types of GAGs include hyaluronic acid, chondroitin sulfate, dermatan sulfate, keratan sulfate, heparin sulfate.

The invention provides methods of use of the compositions if the invention including methods of implanting processed adipose tissue in a subject. Such methods include identifying a subject in need of implantation of processed adipose tissue; identifying a site in a subject in need of implantation of processed adipose tissue; and implanting the processed adipose tissue in the subject at the identified site. The methods of implantation can be performed using any composition provided herein or made by the methods provided herein. Methods for implantation can further include methods for monitoring a subject for persistence of the implanted material and/or infiltration of cells into the implant and/or the tolerance of the subject to the implanted material. Monitoring can be performed using any known method such as the methods provided herein.

The invention provides methods for preparation of processed adipose tissue (PAT), particularly processed human adipose tissue (PhAT), including sequentially obtaining mammalian tissue comprising solid adipose, such as subcutaneous adipose tissue, isolating the adipose from the non-adipose material in the tissue; for example by scraping, and manipulating the adipose with one or more buffers sequentially to promote lipid and cell removal to prepare processed adipose tissue; or by treatment with supercritical carbon dioxide ($CO_2$) (see, e.g., U.S. Pat. No. 4,466,923, incorporated herein by reference). The mammalian adipose tissue can be obtained from any mammal, most conveniently from larger mammals to provide sufficient starting material.

Buffers for use during the manipulation of the isolated adipose include buffers of physiological pH and ionic strength, such as phosphate buffered saline (PBS) or physiological saline. Buffers can further compounds such as weak acid, a weak organic acid, a non-ionic detergent, or a bile acid, or a combination thereof, to promote decellularization or lipid extraction of the solid adipose.

The invention provides methods in which the isolated adipose can also be contacted with one or more nucleases, e.g., DNases and RNases, to promote degradation of nucleic acids that may be present in the material. Contacting with nucleases can be performed at any step, but is preferably performed after the decellularization steps as the decellularization process may break open cells, releasing nucleic acids making them more available for degradation.

The processed adipose tissue provided by the invention can also include biopolymers and biopolymer cross-linking agents to generate molecular cross-links within and between the biopolymer molecules, in addition to between the biopolymer and the adipose tissue derived material to create a biopolymer scaffold. These biopolymers, can consists of, but are not limited to, hyaluronic acid, chondroitin sulfate, collagen, elastin, and laminins.

The invention provides methods for forming the processed adipose tissue of the invention into particles, for example to facilitate administration. The invention provides methods for optionally combining the processed adipose tissue with one or more cross-linking agents and/or a biopolymer scaffold. The biopolymer scaffold can be previously cross-linked (e.g., cross-linked hyaluronic acid), or include functional groups to allow the biopolymer to form a cross-linked structure in the absence of any further agents (e.g., functionalized chondroitin sulfate). Alternatively, the biopolymer scaffold can require the use of cross-linking agents and polymerization initiators. Polymerization initiators can include chemical initiators or light. The invention provides methods for polymerization of the biopolymer scaffold.

The invention further provides compositions made by any of the methods of the invention, including any processing intermediates.

The invention further provides for the use of any of the compositions of the instant invention as biomaterials, including any processing intermediates, for example for tissue reconstruction or restoration. The invention provides the compositions of the instant invention in an appropriate carrier for administration (e.g., saline, buffers, with or without antibiotics, anesthetics, growth factors, or other extracellular matrix components, or a material that provides viscosity for greater ease of injection.)

Definitions

As used herein, "acellular" is understood as a material that contains no cells, viable or non-viable, whole or fragments, or sufficiently few cells or cellular material such that the cells present are not sufficient to generate an immune response in the subject into which the material is implanted. Cells may be removed from source tissue, for example, by mechanical or chemical methods, or a combination thereof.

An "acellular adipose biocompatible biomaterial", also referred to as "processed adipose tissue" or "PAT" is understood as a composition derived from adipose tissue obtained from a donor, for example from a live donor (e.g., autologous donation, byproduct of cosmetic surgical procedure such as liposuction or abdominoplasty) or tissue bank (e.g., live donor, cadaver donor). The composition can be derived from subcutaneous fat, visceral fat, white fat, brown fat, a mixed cell population including fat tissue (e.g., a lipoaspirate) or any combination thereof. In a first step, the adipose separated from the non-adipose material in the tissue sample, e.g., by scraping the adipose from the dermis or surrounding organ, partitioning the lipoaspirate, etc. to prepare isolated adipose. The isolated is treated with chemical and/or mechanical methods to remove the fat cells and the lipid components. The material is preferably treated to kill any remaining cells not removed by the process prior to implantation in a subject. The material is preferably treated with one or more nucleases, e.g., DNase and/or RNase, to destroy any potentially immunogenic nucleic acids that may be present in the material. As the material is acellular, it is non-immunogenic. Therefore, the composition can be implanted non-autologously. Further, the material can be used as an "off the shelf" product for use in reconstructive and cosmetic surgery procedures. The composition can be combined with other materials prior to implantation into the subject, including other biomaterials or biopolymers, and cells or cellular material, for example autologous or donor cells including but not limited to adult stem cells, mesenchymal stem cells, adipose derived mesenchymal stem cells, embryonic stem cells, induced pluripotent stem cells, fibroblasts, adipocytes.

The terms "active agent," and "biologically active agent" are used interchangeably herein to refer to a chemical or biological compound that induces a desired pharmacological, physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent" and "drug" are used, then, it is to be understood that applicants intend to include the active agent per se as well as pharmaceutically acceptable, pharmacologically active salts, esters, amides, prodrugs, metabolites, analogs, etc.

As used herein, "anesthetic" is understood as an agent that provides a lack of sensation or sensitivity. In the context of the instant invention, an anesthetic is typically a locally acting anesthetic, providing a reduction of sensation or sensitivity to the tissue contacted by the agent. Local anesthetics include, but are not limited to benzocaine, chloroprocaine, cocaine, cyclomethycaine, dimethocaine/larocaine, propoxycaine, procaine/novocaine, proparacaine, tetracaine/amethocaine, articaine, bupivacaine, carticaine, cinchocaine/dibucaine, etidocaine, levobupivacaine, lidocaine/lignocaine, mepivacaine, piperocaine, prilocaine, ropivacaine, trimecaine, saxitoxin, and tetrodotoxin.

As used herein, "antibiotic" is understood as an agent to destroy or kill pathogens and/or infectious agents, including, but not limited to, bacteria and viruses. Antibiotics include, but are not limited to, those which target the bacterial cell wall (penicillins, cephalosporins), or cell membrane (polymixins), or interfere with essential bacterial enzymes (quinolones, sulfonamides) usually are bactericidal in nature. Those which target protein synthesis, such as the aminoglycosides, macrolides and tetracyclines, are usually bacteriostatic.

As used herein, "antioxidant" is understood as an agent that reduces or prevents the formation of, or reduces or prevents the damage caused by superoxides and/or oxide radicals. Antioxidants include free radical scavengers. Many vitamins, including vitamin C and vitamin E are antioxidants. Other antioxidants include, but are not limited to, ascorbic acid (vitamin C), glutathione, melatonin, and tocopherols and tocotrienols (e.g., vitamin E). Antioxidants for use in the invention are preferably biocompatible.

As used herein, "autologous" transplantation, donation, and the like is understood as a procedure in which the source of adipose tissue for implantation into the subject is derived from the same subject. Autologous transplantation or donation can include processing of the tissue between harvesting of the tissue from the subject and re-implantation of the tissue into the subject.

As used herein, a "basement membrane" is understood as is a thin sheet of fibers that underlies the epithelium, which lines the cavities and surfaces of organs, or the endothelium, which lines the interior surface of blood vessels. The primary function of the basement membrane is to anchor down the epithelium to its loose connective tissue underneath. This is achieved by cell-matrix adhesions through cell adhesion molecules (CAMs). Basement membrane proteins are secreted by either epidermal or endothelial cells, which usually define a border in the body, usually "in vs out", to define a lumen in the body, e.g., gut or bladder has an epidermal basement membrane, defining or separating the inside empty space from the outside; or for endothelial cells which border the lumen of a blood vessel, defining inside vs outside. Adipose does not define a space or serve to separate an inside vs outside of a body cavity or organ. Adipose ECM has basement membrane only to the extent that it has blood vessels, which have basement membranes (and fat as a lot of microvessels). The adipose itself does not include a basement membrane. Unlike dermis, naturally occurring fat does not include a substantial amount of BM, as does dermis. Naturally occurring adipose tissue is composed primarily of lipid. After preparation of the processed adipose tissue material described herein, the material is essentially free of basement membrane, e.g., 80% or more, 90% or more, 95% or more, 97% or more, 98% or more, 99% or more of the material that defines a basement membrane is removed from the processed adipose tissue. Moreover, as used herein, the basement membrane is typically considered to be capable of enclosing or partitioning a space.

The composition of the basement membrane is well defined. Therefore, one of skill in the art would be able to determine materials that were derived from a basement membrane. The basement membrane is the fusion of two basal laminae. It consists of an electron-dense membrane called the lamina densa, about 30-70 nanometers in thickness, and an underlying network of reticular collagen (type III) fibrils (its precursor is fibroblasts) which average 30 nanometers in diameter and 0.1-2 micrometers in thickness. This type III collagen is of the reticular type, in contrast to the fibrillar collagen found in the interstitial matrix. In addition to collagen, this supportive matrix contains intrinsic macromolecular components. The Lamina Densa (which is made up of type IV collagen fibers; perlecan (a heparan sulfate proteoglycan) coats these fibers and they are high in heparan sulfate) and the Lamina Lucida (made up of laminin, integrins, entactins, and dystroglycans) together make up the basal lamina Lamina Reticularis attached to basal lamina with anchoring fibrils (type VII collagen fibers) and microfibrils (fibrilin) is collectively known as the basement membrane.

The term "bile acid" is understood as a steroid acids found predominantly in the bile of mammals. Bile acids can act as detergents and surfactants. Bile acids include, but are not limited to taurocholic acid, glycocholic acid, cholic acid, chenodeoxycholic acid, deoxycholic acid, and lithocholic acid.

The term "biocompatible" when used in relation to polymers are art-recognized. For example, biocompatible polymers include polymers that are neither themselves toxic to the host at the concentrations and quantities used (e.g., an animal or human), nor degrade (if the polymer degrades) at a rate that produces monomeric or oligomeric subunits or other byproducts at toxic concentrations in the host. In certain embodiments of the present invention, biodegradation generally involves degradation of the polymer in an organism, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in certain embodiments, toxicology of a biodegradable polymer intended for in vivo use, such as implantation or injection into a patient, may be determined after one or more toxicity analyses. It is not necessary that any subject composition have a purity of 100% to be deemed biocompatible; indeed, it is only necessary that the subject compositions be biocompatible as set forth above. Hence, a subject composition may comprise polymers comprising 99%, 98%, 97%, 96%, 95%, 90%, 85%, 80%, 75%, 70%, 60%, 50% or even less of biocompatible polymers, e.g., including polymers and other materials and excipients described herein, and still be biocompatible.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner the sample is degraded in 1M NaOH at 37° C. until complete degradation is observed. The solution is then neutralized with 1M HCl. About 200 μL of various concentrations of the degraded sample products are placed in 96-well tissue culture plates and seeded with human gastric carcinoma cells (GT3TKB) at $10^4$/well density. The degraded sample products are incubated with the GT3TKB cells for 48 hours. The results of the assay may be plotted as % relative growth vs. concentration of degraded sample in the tissue-culture well. In addition, polymers, polymer matrices, and formulations of the present invention may also be evaluated by well-known in vivo tests, such as subcutaneous implantations in rats to confirm that they do not cause significant levels of irritation or inflammation at the subcutaneous implantation site.

Biocompatible materials can also include naturally derived products appropriate for implantation into a subject, such as the acellular adipose biomaterial provided herein.

As used herein, "biocompatible biomaterial" are materials that can be used for tissue reconstruction, e.g., facial reconstruction, breast reconstruction, injection laryngoplasty; treating HIV protease-induced lipoatrophy; cosmetic surgery e.g., breast, buttock, calf, pectoralis, lip, and cheek augmentation, reversing wrinkles and filling in defects including scars, traumatic injury, congenital defects, surgical scars, burns, and defects from tumor resection, that are acceptable for use in a mammal, preferably in a human subject.

As used herein, a "caspase inhibitor" is a class of protease inhibitors that prevent the action of the caspase proteases, also known as cysteine-aspartic acid proteases, which are involved in apoptosis, necrosis, and inflammation. Caspase inhibitors include, but are not limited to Caspase Inhibitor I, II, III, Caspase 1 Inhibitor I, II, III, Caspase 2 Inhibitor, Caspase 3 Inhibitor, etc.

"Contacting" as used herein is understood as bringing two or more components into sufficient proximity (e.g. a biocompatible polymer, a cross-linking agent, a surfactant, and an adipose cell; subcutaneous adipose tissue and peracetic acid) for sufficient time and under appropriate condition of temperature, pressure, pH, ionic strength, etc. to allow for the interaction of the two or more components, e.g., formation of a gelled biopolymer matrix including adipose cells; decellularization of adipose tissue. Contacting in the context of the invention can occur in a reaction vessel such as a tube, or in a subject in a body cavity to be filled with a composition of the invention.

"Cross-linked" as used herein refers to a composition containing intermolecular cross-links and optionally intramolecular cross-links arising from the formation of covalent bonds, ionic bonds, hydrogen bonding, or any combination thereof "Cross-linkable" refers to a component or compound that is capable of undergoing reaction to form a cross-linked composition.

As used herein, a "cross-linker" or a "cross-linking agent" and the like are understood as a compound that includes at least two reactive groups to allow for the formation of a covalent linkage, i.e., a cross-link, between two other molecules with compatible reactive groups. Cross-linking reagents contain reactive ends to specific functional groups (primary amines, sulfhydryls, etc.) on proteins or other molecules. Several chemical groups that may be targets for reactions in proteins and peptides are readily available, allowing them to be easily conjugated and studied using cross-linking methods. In certain embodiments, the cross-linker is used for the formation of a cross-link between two naturally occurring biopolymers, e.g., such as those present in the processed adipose tissue of the instant invention. Such cross-linkers include, but are not limited to, carbodiimide (EDC), hexamethylene diisocyanate (HMDC), gluteraldehyde, proanthocyanidin, ribose, threose, and lysyl oxidase, carbodiimide (e.g., N-(3-dimethylaminopropyl)-N-ethylcarbodiimide (EDC)), N-hydroxysuccinimide (NHS), polyepoxy ethers, divinyl sulfone (DVS), genipin, polyaldehyde and diphenylphosphoryl azide (DPPA), genipin, epoxy compounds, dialdehyde starch, glutaraldehyde, formaldehyde, dimethyl suberimidate, carbodiimides, succinimidyls, diisocyanates, hexamethylene diisocyanate (HMDC), and acyl azide; or any combination thereof (e.g., 2, 3, 4, 5, 6, 7, 8, 9, 10, or more cross-linkers). A "biopolymer cross-linker" and the like is understood as a cross-linker for use with a biopolymer such as artificial biopolymers or chemically modified naturally occurring biopolymers, i.e., not a biopolymer present in adipose tissue. Such biopolymers include, but are not limited to, hyaluronic acid, hydrogels, and other cross-linkable hydrophilic, charged, or otherwise covalently cross-linkable materials discussed herein. The selection of an appropriate cross-linker for use with biopolymers not present in adipose tissue are discussed herein.

The polymerizable agent of the present invention may comprise monomers, macromers, oligomers, polymers, or a mixture thereof. The polymer compositions can consist solely of covalently crosslinkable polymers, or ionically crosslinkable polymers, or polymers crosslinkable by redox chemistry, or polymers crosslinked by hydrogen bonding, or any combination thereof. The polymerizable agent should be substantially hydrophilic and biocompatible.

As used herein, "detecting", "detection" and the like are understood that an assay or method performed for identification of a specific analyte in a sample. The amount of analyte detected in the sample can be none or below the level of detection of the assay or method.

The term "gel" refers to a state of matter between liquid and solid, and is generally defined as a cross-linked polymer network swollen in a liquid medium. Typically, a gel is a two-phase colloidal dispersion containing both solid and liquid, wherein the amount of solid is greater than that in the two-phase colloidal dispersion referred to as a "sol." As such, a "gel" has some of the properties of a liquid (i.e., the shape is resilient and deformable) and some of the properties of a solid (i.e., the shape is discrete enough to maintain three dimensions on a two dimensional surface). "Gelation time," also referred to herein as "gel time," refers to the time it takes for a composition to become non-flowable under modest stress. This is generally exhibited as reaching a physical state in which the elastic modulus $G'$ equals or exceeds the viscous modulus $G''$, i.e., when tan (delta) becomes 1 (as may be determined using conventional rheological techniques).

As used herein, "growth factor" is understood as a naturally occurring substance capable of stimulating cellular growth, proliferation and cellular differentiation. Usually it is a protein or a steroid hormone. Growth factors are important for regulating a variety of cellular processes including cell growth, differentiation, migration, and angiogenesis. Growth factors typically act as signaling molecules between cells. Examples are cytokines and hormones that bind to specific receptors on the surface of their target cells. Growth factors include, but are not limited to, bone morphogenetic proteins (BMPs), epidermal growth factor (EGF), erythropoietin (EPO), fibroblast growth factor (FGF), granulocyte-colony stimulating factor (G-CSF), granulocyte-macrophage colony stimulating factor (GM-CSF), growth differentiation factor-9 (GDF9), hepatocyte growth factor (HGF), insulin-like growth factor (IGF), myostatin (GDF-8), nerve growth factor (NGF) and other neurotrophins, platelet-derived growth factor (PDGF), thrombopoietin (TPO), transforming growth factor alpha (TGF-α), transforming growth factor beta (TGF-β), and vascular endothelial growth factor (VEGF).

"Hyaluronic acid" (HA) (also known as "hyaluronan" or "hyaluronate") is a non-sulfated glycosaminoglycan distributed widely throughout connective, epithelial, and neural tissues. It is one of the chief components of the extracellular matrix, contributes significantly to cell proliferation and migration, and may also be involved in the progression of some malignant tumors. The repeating disaccharide unit of HA is $(-4GlcUA\beta1-3GlcNAc\beta1-)_n$. Hyaluronic acid can be 25,000 disaccharide repeats in length. Polymers of HA can range in size from 5 to 20,000 kDa in vivo. Hyaluronic acid for use in the invention can have a molecular weight of about 5, 10, 25, 50, 100, 500, 1000, 2000, 5000, 7500, 10,000, 15,000, or 20,000 kDa, or any range between any of the two molecular weights provided. The specific size of the HA to be used is a matter of choice of the end user. For example, it is well understood that higher molecular weight HA has better viscosity for many applications. Lower molecular weight HA is angiogenic, however, lower molecular weight HA also produces a stronger inflammatory reaction than higher molecular weight HA. Such considerations are well understood by those of skill in the art.

As used herein, a "hydrogel" is understood as a hydrophilic cross-linked polymer capable of containing a large volume fraction of water. More preferably hydrogels according to the present invention can contain greater than about 70-90 volume % water. When a hydrophilic polymer is formed in situ, it may inherently acquire water from its environment or from solutions used to create the hydrogel.

As used herein, "isolated" particularly as used in "isolated adipose" is understood as separating the non-adipose tissue or cells from the adipose extracellular matrix, tissue, or cells to allow for preparation of one or more of the biomaterials of the instant invention. "Isolated adipose" can include solid isolated adipose, e.g., from tissue samples e.g., such as subcutaneous fat, or liquid isolated adipose, e.g., from lipoaspirate. Isolation does not require that the material is completely free of non-adipose material. Isolated adipose is understood as containing at least 70%, 80%, 85%, 90%, 95%, or 98% adipose cells, tissue, extracellular matrix, etc. For example, adipose can be isolated from a tissue sample including subcutaneous fat by scraping. Adipose can be isolated from lipoaspirate by density using methods known in the art.

As used herein, "kits" are understood to contain one or more components for use in a method of the invention, in appropriate packaging or with instructions for use.

As used herein, "lipoaspirate" is an otherwise disposable byproduct of cosmetic surgery procedures such as liposuction.

As used herein, "mammal" is understood as any animal of the class mammalian Mammal is understood to include, but is not limited to human and non-human primates, pigs, dogs, cats, cows, mice, rats, horses, and rabbits.

As used herein, "manipulating" is understood as manually (e.g., like kneading bread) or mechanically (e.g., using a mixer, homogenizer, or blender) to work, press, or divide a mass of non-liquid material, e.g., adipose, to contact the material throughout with another material, e.g., a buffer, a dry material, a solvent, a supercritical fluid, an enzyme etc Manipulating can be performed, for example, to promote decellularization and/or lipid removal from adipose.

As used herein, "mincing" is understood as processing material, e.g., fat, for example by grinding or chopping material, or extruding material through a die, optionally repeatedly, to provide material that is finely divided. The material is preferably sufficiently fine to allow the agents contacted with the lipid, e.g., acid, detergent, buffer, cross-linking agent, to permeate the material. It is understood that the process of isolation of lipid from tissue necessarily results in providing smaller pieces of tissue.

"Non-ionic detergent" as used herein is understood to include, for example, ethoxylated fatty alcohol ethers and lauryl ethers, ethoxylated alkyl phenols, octylphenoxy polyethoxy ethanol compounds, modified oxyethylated and/or oxypropylated straight-chain alcohols, polyethylene glycol monooleate compounds, polysorbate compounds, and phenolic fatty alcohol ethers. More particularly preferred are Triton® X-100, Triton® X-114, Pluronics from BASF (such as those listed as surfactants below) Tween® 20, Tween® 80, from ICI Americas Inc., Wilmington, Del., which is a polyoxyethylated (20) sorbitan monolaurate, Iconol™ NP-40, from BASF Wyandotte Corp. Parsippany, N.J., which is an ethoxylated alkyl phenol (nonyl); octyl-glucoside, and octyl-thioglucoside.

As used herein, "nuclease" is understood as an enzyme that digests one or more nucleic acids, e.g., DNA and RNA. Nucleases include, but are not limited to, oligonucleotidase, deoxyribonuclease I, II, IV, restriction enzymes, UVrABC endonuclease, RNase III, RNase H, P, A, T1, and micrococcal nuclease. The nuclease for use in the processed adipose tissue of the invention is preferably biocompatible and/or becomes inactivated or can be inactivated prior to delivery of the processed adipose tissue to the subject.

"Obtaining" is understood herein as manufacturing, purchasing, or otherwise coming into possession of.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers for use in the invention may be in the form of a sterile injectable preparation, for example, as a sterile injectable aqueous or oleaginous suspension. This suspension may be formulated according to techniques known in the art using suitable dispersing or wetting agents (such as, for example, Tween® 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

As used herein, "plurality" is understood to mean more than one. For example, a plurality refers to at least two, three, four, five, 10, 25, 50, 100 or more.

"Polyethylene glycol" (PEG) (also known as poly(ethylene oxide) (PEO) or polyoxyethylene (POE)) has the formula $HO-(CH_2-CH_2-O-)_n-H$ and are typically linear (i.e., unbranched) molecules. Polyethylene glycol for use in the compositions and methods of the instant invention have a molecular weight of about 1000 MW to 10,000 MW.

A polymerizable mixture as used herein is any suitable polymerizable polymer, monomer, or mixture of monomers and polymers that forms: a covalently crosslinked network, with or without the presence of a polymerization initiator, an ionically crosslinked network, or blends of covalently and ionically crosslinked networks. Polymerizable mixtures in accordance with the present invention must be able to form polymerized networks that are non-toxic to the cells being encapsulated, or the tissue or subject into which the material is to be implanted.

A photopolymerizable polymer is any suitable polymer that forms a covalently crosslinked network using radiation provided by an external source, or blends of covalently and ionically crosslinkable or hydrophilic polymers which, when exposed to radiation from an external source, form semi-interpenetrating networks having cells suspended therein. Photopolymerizable mixtures in accordance with the present invention must be able to form polymerized networks that are non-toxic to the cells being encapsulated.

A polymerization initiator is any substance that initiates crosslinking of the polymer to form a hydrogel network, and includes redox agents, divalent cations such as calcium, and substances that form active species when exposed to visible light and/or UV radiation. A photoinitiator is a specific type of polymerization initiator that generates an active species when exposed to UV light and/or visible light, and can be used to initiate polymerization (i.e., crosslinking) of the photopolymerizable mixtures. Polymerization initiators and photoinitiators in accordance with the present invention must be non-toxic to the cells being encapsulated when used in the amounts required to initiate crosslinking of the polymerizable mixtures.

A hydrogel for encapsulating living cells is a hydrophilic polymer network with a high water content. Such hydrogels in accordance with the present invention, may have, for example, a water content greater than about 70-90%. Such hydrogels in accordance with the present invention are non-toxic to the encapsulated cells and permit the movement of nutrients to the cells, and waste products away from the cells, through the polymer network.

A "polymerizing initiator" refers to any substance or stimulus that can initiate polymerization of monomers or macromers by free radical generation. Exemplary polymerizing initiators include electromagnetic radiation, heat, and chemical compounds.

The process of "promoting decellularization and lipid extraction" is understood as chemical or physical treatment and/or manipulation of a sample, such as a tissue sample, to remove cells and lipids from the material. The process can include serial rounds of washing and manipulation of the sample in the presence of one or more buffers.

"Providing," refers to obtaining, by for example, buying, making, or otherwise coming into possession of.

"Securely attached viable cells" are understood as living, adherent cells that remain attached to the processed adipose tissue, for example, using routine methods of rinsing cells to exchange growth media. Securely attached viable cells remain attached to the processed adipose tissue, for example, through routine washing methods to image cells attached to the matrix using the methods such as those provided in the examples below. It can be determined that viable cells are securely attached, or if a material allows for secure attachment of cells by performing routine cell staining methods (e.g., immunofluorescence, tyrpan blue, etc.) and determining that 50% or more, 60% or more, 70% or more, 80% or more, 90% or more, or 95% or more of the viable cells originally attached to the processed adipose tissue remain attached after the rinsing and/or washing steps used in cell culture, immunofluorescence staining, or other cell staining and manipulation methods provided herein.

As used herein, a "solution" means a solution, a suspension, or a colloid.

The term "space," is used herein to described the location of where a composition of the instant invention is injected or implanted to solidify, and is defined broadly and may include a cavity formed in a mold, a cavity surgically formed in tissue, or a naturally existing cavity in tissue that can be surgically accessed, a wrinkle or other tissue aberration to be repaired using the compositions and methods of the invention.

As used herein, "subject" is understood as an animal, preferably a mammal such as a mouse, rat, dog, cat, monkey, cow, pig, or a human or non-human primate. A human subject can also be known as a patient.

As used herein, a "substantial immune response" is understood as an immunological response of a subject after implantation of a processed adipose tissue of the invention that requires intervention by a medical professional (e.g., need for removal of the processed adipose tissue, administration of immunosuppressive drugs); or results in substantially reduced lifetime of the implanted processed adipose tissue, for example the duration of the implanted processed adipose tissue is decreased by 50% or more, at least 60% or more, at least 70% or more, at least 80% or more, or at least 90% or more, and wherein the implanted processed adipose tissue is infiltrated with at least one type of inflammatory cell including, but not limited to, macrophages, neutrophils, and eosinophils. A substantial immune response does not include temporary and transient (e.g., one week or less, 6 days or less, 5 days or less, 4 days or less, 3 days or less, 2 days or less, or one day or less) of general redness, irritation, and swelling at the site of implantation that is reduced over time, and may not be a response to the implanted tissue per se, but instead to the disruption of the skin or otherwise adjacent tissue due to the disruption or stretching of the skin or tissue associated with implantation.

"Surfactant" as used herein is a composition for helping emulsification of fat tissue in the described biomaterial, hydrogel, or other biomaterial solution comprising a straight chain polyether surfactant having an HLB (hydrophilic-lipophilic balance) value greater than or equal to 18 or any of combination, which is proved to be safe for clinical use.

Straight chain polyether surfactants are available from commercial sources including, but not limited to, BASF Wyandotte Corp (Wyandotte, Mich.) as "Pluronic™". The HLB of a surfactant is known to be a major factor in determining the emulsification characteristics of a polyether surfactant. In general, surfactants with lower HLB values are more lipophilic, while surfactants with higher HLB values are more hydrophilic. The HLB values of various poloxamines and poloxamers are provided by BASF Wyandotte Corp.

Suitable straight chain polyether surfactants having an HLB value greater than or equal to 18, include for example but are not limited to Pluronic $F_{38}$™ (BASF) having a HLB of 31 and average molecular weight (AMW) of 4700; Pluronic $F_{68}$™ (BASF) having a HLB of 29 and AMW of 8400; Pluronic 68LF™ (BASF) having a HLB of 26 and AMW or 7700; Pluronic $F_{77}$™ (BASF) having a HLB of 25 and AMW of 6600; Pluronic $F_{87}$™ (BASF) having a HLB of 24 and AMW of 7700; Pluronic $F_{88}$™ (BASF) having a HLB of 28 and AMW or 11400; Pluronic $F_{98}$™ (BASF) having a HLB of 28 and AMW of 13000; Pluronic $F_{108}$™ (BASF) having a HLB of 27 and AMW of 14600; Pluronic $F_{127}$™ (BASF) having a HLB of 22 and AMW of 12600; Pluronic $L_{35}$™ (BASF) having a HLB of 19 and AMW of 1900; Tetronic 707™ (BASF) having a HLB of 27 and AMW of 12200; Tetronic 908™ (BASF) having a HLB of 31 and AMW of 25000. The preferred straight chain poly (ethylene oxide-propylene oxide-ethylene oxide) (PEO-PPO-PEO) block copolymers having HLB value greater than or equal to 18, Pluronic surfactants, are Pluronic $F^{38}$™, Pluronic $F_{68}$™ Pluronic 68LF™, Pluronic $F_{77}$™, Pluronic $F_{87}$™, Pluronic $F_{88}$™, Pluronic $F_{98}$™, Pluronic $F_{108}$™, and Pluronic $F_{127}$™. More preferred Pluronic surfactants are Pluronic $F_{127}$™

To obtain the required HLB of fat tissue, polyether surfactants or polyether surfactants in combination in the aqueous composition is from about 2.0 to 10.0 weight percent. More preferably, the total combined amounts range from 4.0 to 8.0 weight percent.

"Weak Acid" as used herein is understood herein as an acid that does not dissociate completely in solution, for example, peracetic acid (PAA), acetic acid, boric acid, and phosphoric acid.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

"At least" a certain value is understood as that value or more. For example, "at least 10," is understood as "10 or more"; "at least 20" is understood as "20 or more." As used herein, "less than" a specific value is understood to mean that value and less. For example "less than 10" is understood to mean "10 or less."

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE FIGURES

FIGS. 12A-C show results from a two-week in vivo rat subcutaneous implantation study. Gross (top) and histological (bottom) images of adipose ECM after 2 weeks of implantation by subcutaneous injection for A) uncrosslinked control, B) 5 mM EDC crosslinked, and C) 1% HMDC in Tween-20 crosslinked ECM.

DETAILED DESCRIPTION AND PREFERRED EMBODIMENTS

Figure 1A:
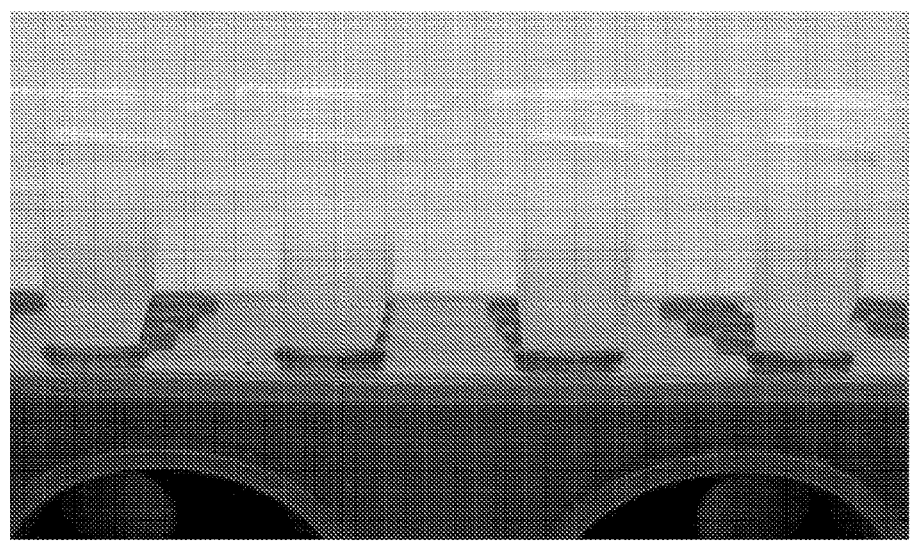
FIGS. 1A-C shows lipoaspirate adipose tissue for implantation. A) shows a lipid and aqueous PEG mixture. The far left tube contains no surfactant. Phase separation is evident. Moving to the right, increased concentrations of surfactant have been added demonstrating improved emulsification; B) shows 10% w/v PEG dissolved in varying ratios of lipoaspirate and HA (10%-50%); and C) shows an athymic mouse after subcutaneous injections of lipoaspirate and PEG and HA.

The invention provides biocompatible biomaterials, methods for preparation of the biomaterials, and methods for implantation of the biomaterials of the instant invention.

In the field of reconstructive surgery there is a significant need for appropriate soft tissue replacement. Adipose tissue continues to be the tissue of choice in repairing soft tissue defects due to trauma and surgical resections for tumors or congenital defects. Current autologous fat transfer techniques, however, have a number of limitations. The persistence of fat transfer varies widely with reports of anywhere between 30-90% in the literature. Persistence is often surgeon, technique, and patient dependent. Such loss of persistence requires multiple procedures to maintain the desired correction. The donor site morbidity associated with autologous fat transfer is also a significant concern. In addition, implanted adipose tissue often leads to post-operative calcifications. This is of particular importance for women with a history of breast cancer undergoing breast reconstruction following mastectomy, as this may interfere with mammography readings and result in multiple, unnecessary breast biopsies and anxiety. Finally, for many HIV patients suffering from lipodystrophy, or for patients undergoing chemotherapy and radiation for cancer, the associated cachexia leaves them without the adipose volume they would require for autologous fat transfer. For these reasons, a predictable, "off-the-shelf" material that retains the mechanical and biological properties of adipose tissue would be ideal for the reconstruction of soft tissue defects and soft tissue augmentation.

One of the aims of regenerative medicine is to provide tissue substitutes. While biomaterials and cells are often employed to regenerate new tissues, these methods tend to be costly and take significant time to form the new tissue. Recently, tissue substitutes have been created from processed skin, bone, bladder, vessels, intestinal and amniotic membranes and are in clinical use for a variety of applications. Various processing methods have been employed to decellularize tissues, leaving behind the extracellular matrix (ECM), which consists of a unique, tissue specific aggregation of the structural and functional proteins ideally suited to support and maintain cells that make up a given tissue. (Reing, 2009. Tissue Engineering 15:605.)

Previous studies have shown that the ECM components, glycoproteins, growth factors, and gylcosaminoglycans (GAGs) found specifically in subcutaneous adipose tissue have the potential to induce adipogenesis. We have investigated various methods to process adipose tissue in order to utilize the inherent bioactivity of subcutaneous adipose tissue to create instructive matrices for adipose tissue reconstruction. The methodologies for the fat tissue treatment depend on removal of cells and lipids that cause inflammatory reactions and local toxic reactions, respectively. The final, processed human adipose tissue (PhAT) is acellular and contains little to no lipid remnants, yet retains the native architecture and bioactivity of adipose tissue. This PhAT provides both volume and a scaffold for in situ tissue formation to be used for soft tissue reconstruction and augmentation.

The first class of biocompatible biomaterials provided by the instant invention, cell based biocompatible biomaterials, includes a combination of biomaterial (water, frequently in the form of a hydrogel), and lipid (fat)-soluble molecules in the presence of a surfactant, preferably in conjunction with a scaffold, preferably a biocompatible polymer cross-linkable scaffold. This biomaterial is a fat cell-based biomaterial, and the transplant is preferably from an autologous donor. The extent of mixing can be modified by the surfactant choice and concentration. The fat can be processed as desired and the biomaterial choice can include many of the standard biomaterial components. The importance of combining the water and fat together in the presence of the scaffold is as follows: 1) the scaffold provides a three dimensional framework/scaffold for the cells in the fat to better form tissue (i.e., larger volume); and 2) some biomaterials (i.e., hyaluronic acid) can induce vascularization, which helps fat formation, and provide larger volumes. Since this procedure implantation of the biomaterial of the invention is preferably by injection, multiple injections can be made to build larger tissue structures.

This first class of biocompatible biomaterials allows for the combination of hyaluronic acid, as well as other materials, including hydrogels, with autologous fat through the use of a surfactant system. Such a system allows for the emulsification of hydrophilic biomaterials and lipids into an otherwise immiscible material. The result is an injectable biomaterial with larger volume and enhanced longevity as compared to prior filler materials, thus improving clinical outcome compared to fat or filler transfer alone, while maintaining ease of clinical use and the desired texture.

The invention provides a second class of biocompatible biomaterial which are acellular adipose biocompatible biomaterials also referred to as processed adipose tissue (PAT). The acellular biomaterial is derived from donor adipose tissue, however, as the cellular material is removed from the tissue, it is non-immunogenic and can be used for non-autologous donation. This provides for greater convenience and standardization of biomaterial for use by providing an "off the shelf" biocompatible biomaterial (filler).

The acellular material is produced, for example, by decellularization, preferably chemical decellularization of adipose tissue. Due to the stiffness of the material, mechanical or manual manipulation is performed on the sample at each wash step to insure proper mixing of the processed tissue samples with the wash solutions. Preparation of the acellular adipose biocompatible biomaterial can be accomplished by performance of homogenization and serial washes in sterile saline or buffers for neutralization, preferably followed by serial washes in a solution to further extract the lipid from the cells, for example an organic peroxide such as peracetic acid (about 0.1%-10% v/v, preferably about 0.5% to about 3% v/v, preferably about 1% v/v) or a bile acid such as deoxycholic acid (about 0.1%-10% w/v, preferably about 0.5% to about 2.5% w/v, preferably about 1% w/v). The acid wash is optionally followed by serial washes in a non-ionic detergent such as those provided herein including Triton-X 100 or Tween 20 (about 0.1%-10% v/v, preferably about 0.5% to about 2.5% v/v, preferably about 1% v/v) in a buffer such as phosphate buffered saline (PBS) or in water. Optionally, the bile acid, weak acid, and/or non-ionic detergent washes can be followed by washes in an organic solvent such as dichloromethane/methanol (2:1) to remove the remaining lipid in the material and produce a homogeneous white biological scaffold. Yet another option is to pass the material through a supercritical fluid, such as liquid carbon dioxide, with subsequent evaporation of the carbon dioxide and separation of lipid from the material, thus avoiding the use of toxic organic compounds. The material is then sterilized through any appropriate method including, but not limited to, gamma irradiation and/or treatment with ethylene oxide. This step can be supplemented with any preservation or protective agent in order to reduce damage to the material. The processed adipose tissue is then formed into particles of the desired size, preferably to allow for injection, and optionally mixed with the appropriate biomaterials such as polymerizable biopolymer scaffold with or without one or more cross-linking agents prior to injection into the subject. The material can be freeze-dried, either before or after formation into particles, for storage and re-hydrated prior to use. As needed, the injected material is subjected to a cross-linking activator (e.g., an appropriate wavelength of light) after injection. Such considerations are well understood by those of skill in the art.

Previous studies have shown that the extra-cellular-matrix (ECM) components, glycoproteins, and gylcosaminoglycans (GAGs) found in subcutaneous adipose tissue have the potential to induce adipogenesis (Uriel et al., 2008, The Role of Adipose Derived Protein Hydrogels in Adipogenesis. *Biomaterials.* 29:3712-3719, incorporated herein by reference). Taking advantage of the inherent bioactivity of subcutaneous adipose tissue, the invention provides tissue-derived materials by processing adipose tissue to create instructive matrices for adipose tissue reconstruction. The methodologies for the fat tissue treatment depend on removal of cells and lipids that cause inflammatory reactions and local toxic reactions, respectively. The final, processed adipose tissue (PAT) is acellular and contains little to no lipid remnants, yet retains the native architecture and bioactivity of adipose tissue. Similar to the off-the-shelf acellular dermal product, Alloderm™, which is commonly used for skin replacement and hernia repairs, this PAT would provide both volume and a scaffold for in situ tissue formation in soft tissue reconstruction and augmentation.

As demonstrated herein, subcutaneous adipose tissue can be processed to remove cells and lipids, while still preserving the native architecture of the extra-cellular-matrix. Histology of the processed tissue is void of nucleated cells and the lipid vacuoles seen in unprocessed adipose tissue (e.g., FIGS. 3 and 9).

Figure 5A:
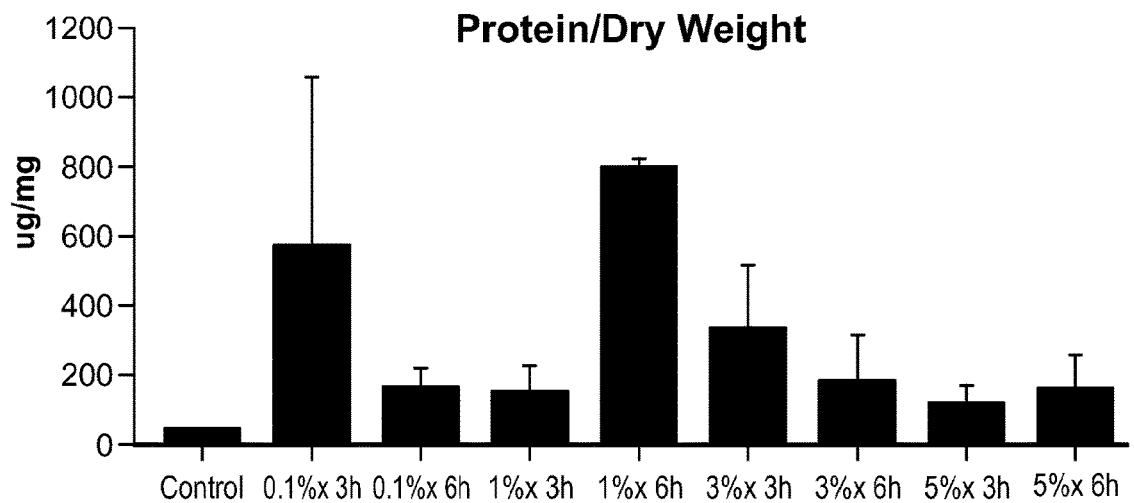
FIGS. 5A-E show results that confirm that the various processing methods are able to remove immunogenic and inflammatory cellular contents including DNA and lipids, but still preserve ECM components, A) the remaining protein content, B) collagen content, and D) GAG content were quantified and compared to control. C) Type I Collagen immunostaining (brown staining) and E) Safrainin-O (red stain) was done on histological samples corroborating the biochemical assays used to quantify the presence of collagen and GAGs.
Figure 5B:
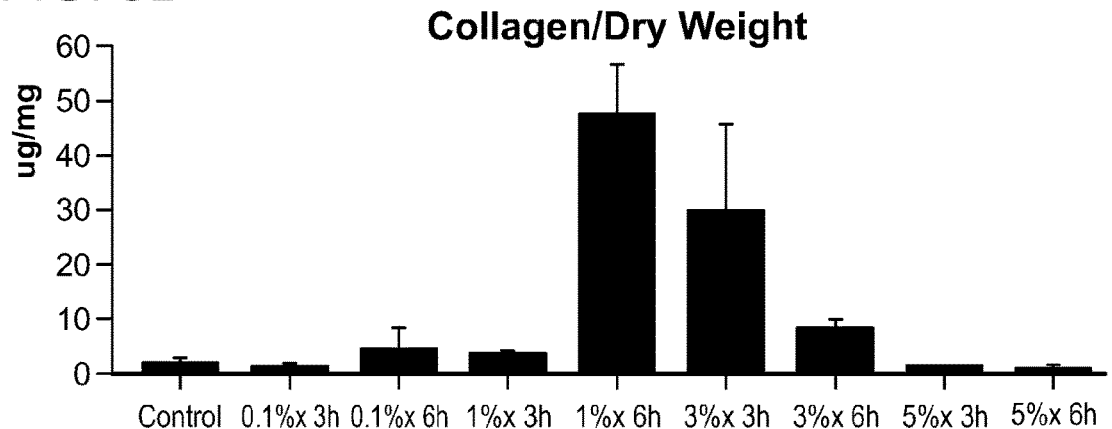
Figure 5C:
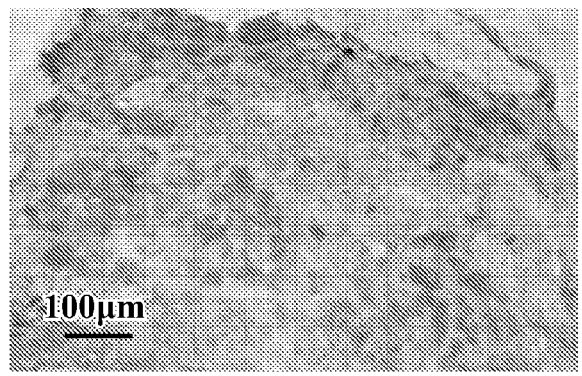
Figure 5D:
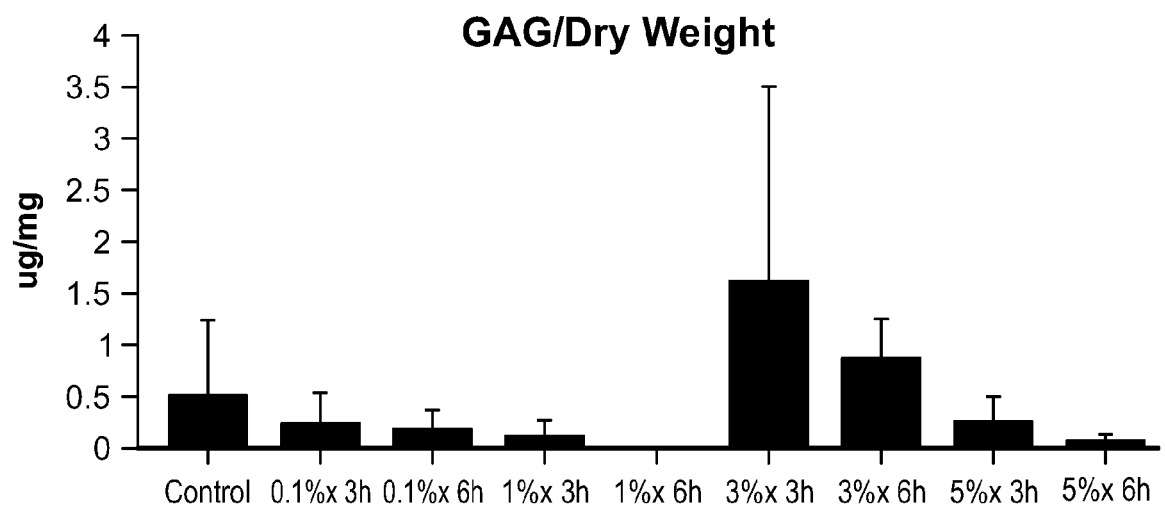

The optimal processing method removes all immunogenic components of tissues, such as cells and cellular debris, including lipids, while maintaining the functional and architectural properties of the ECM. In order to identify the processing method which best preserved ECM, we examined protein, collagen, and glycosoaminoglycan (GAG) content, in addition to rheological properties of PhAT produced from the various processing methods. The protein content remained greatest in the samples treated with PAA and DNAse 1 where adipose tissue was exposed to 1% peracetic acid for 6 hours, 800 µg/mg. In all cases, the protein content was greater than control, 100 µg/mg. This can be explained by the tissue concentration that occurs during processing. Compared to unprocessed fat, where lipid has the greatest contribution to the overall weight of the sample, following processing, a sample of equal weight now consists of concentrated ECM, effectively concentrating the matrix components and proteins in the resulting material. The collagen content of PhAT exposed to 1% for 6 hours and 3% for 3 or 6 hours of peracetic acid (30-45 µg/mg) was significantly greater than control (2 µg/mg, $p<0.05$, FIGS. 5A-C). Exposure to 1% for 3 hours does not sufficiently remove lipids explains why this concentration effect was not seen, and collagen content was similar to control. Exposure to 5% peracetic acid for 3 or 6 hours resulted in collagen content similar to that of control despite being a lipid reduced material, indicating that, in this case, collagen degradation occurred. The results of the collagen assay were confirmed by immunostaining for type I collagen. GAG content was also highest in the PhAT produced with 3% peracetic acid and decreased with increasing or decreasing peracetic acid concentration (FIG. 5C). This was also confirmed histologically with Safranin-O (FIG. 5D).

Figure 6:
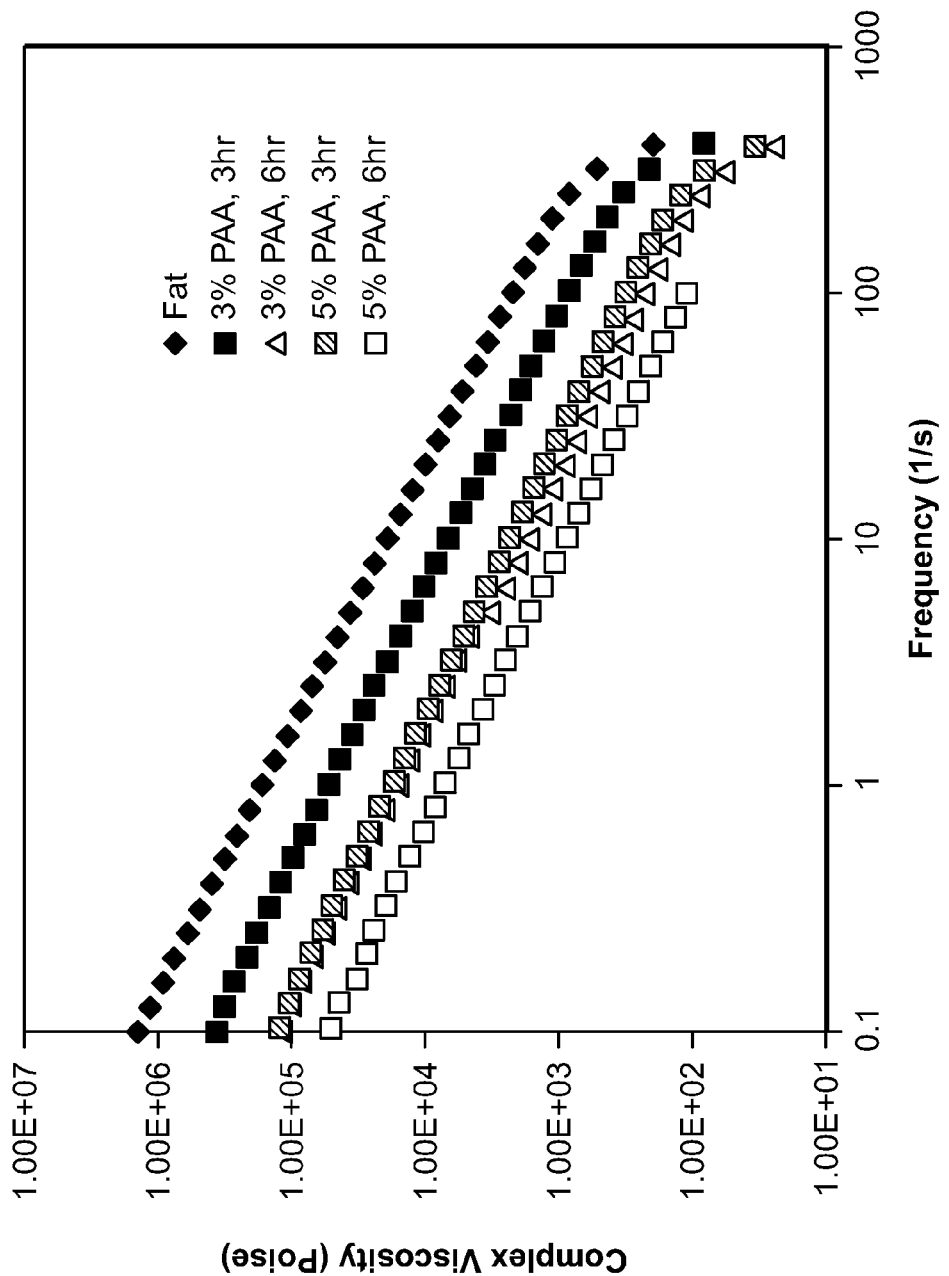
FIG. 6 shows the biomechanical effects on complex viscosity after adipose tissue is exposed to the various processing methods. The complex viscosity decreases as the concentration of PAA used increases.

Further characterization studies of PhAT prepared using PAA and DNase 1 were only conducted on PhATs that were deemed potential candidates for in vivo testing. Therefore, only PhAT with minimal lipid content, 3% and 5%, were included in the remaining studies. As another means of determining which processing method had the least affect on the integrity of the matrix, shear-strain curves were obtained before and after processing. Rheological testing demonstrated that both exposure time and acid concentration affected the complex modulus (FIG. 6). PhAT processed with 3% peracetic acid for 3 hours most closely resembled the pre-processed adipose tissue. When incubated in acid for 6 hours, this PhAT became indistinguishable from the 5%×3 hour PhAT. The greatest decrease in complex modulus occurred when PhAT was produced following exposure to 5% peracetic acid for 6 hours.

The trend seen in the mechanical properties of the different PhATs was also reflected in the cell viability studies of 3% and 5% PhAT seeded with human mesenchymal stem cells. This indicates that the structural changes that were occurring during decellularization accompanied biological changes, affecting cell adherence and viability. Following cell seeding, Live/Dead assay performed at day 1 and day 7. In every case, live cells were present after 24 hours of culturing on the processed adipose tissue. Greater cell viability was found for 3% PAA (3 and 6 hours) PhAT with decreasing viability in 5% PAA×3 hours, and almost minimal viability with 5% PAA×6 hours. By day 7 live cells outnumber dead cells (red nuclear staining) only in PAT processed with 3% PAA.

To function as soft tissue replacement material, biocompatibility and persistence must be demonstrated. To evaluate the in vivo response to and stability of the PhAT, the 3% and 5% PhATs were implanted subcutaneously in rats and monitored over time. Histology at 1 and 3 weeks demonstrated a minimal amount of an inflammatory response (measured by presence of neutrophils, monocytes, and multinucleated giant cells) and no evidence of fibrous encapsulation or tissue necrosis. Representative histological images of the implanted material are shown in FIG. 8C. There was evidence of cellular influx into the tissue, most likely consisting of fibroblasts given their fibroblastic morphology. Full lumen vessels were identified infrequently.

Figure 8A:
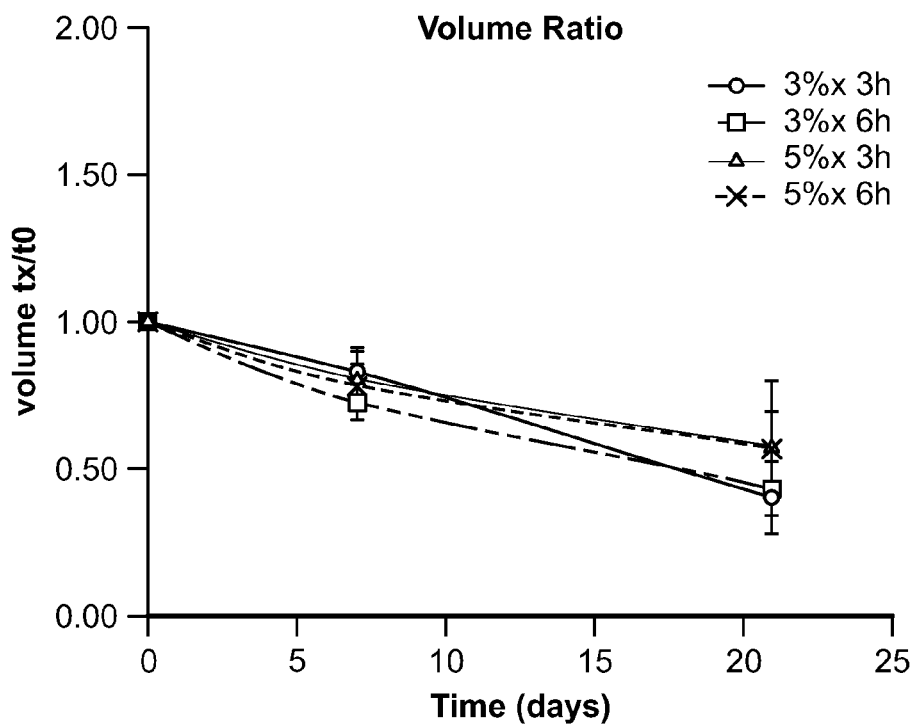
FIGS. 8A-C show the in vivo persistence as measured by A) the volume ratio and B) the height of subcutaneous implants of PAT measured over 21 days in a rat animal model. C) H&E stain of the implanted material at days 7 and 21 showing cellular influx and minimal inflammation as evidenced by darkly staining leukocytes, neutrophils, or macrophages. Though volumetric measurements indicate a decrease in persistence over time, histology demonstrates condensed implant site, possibly indicating tissue integration.
Figure 8B:
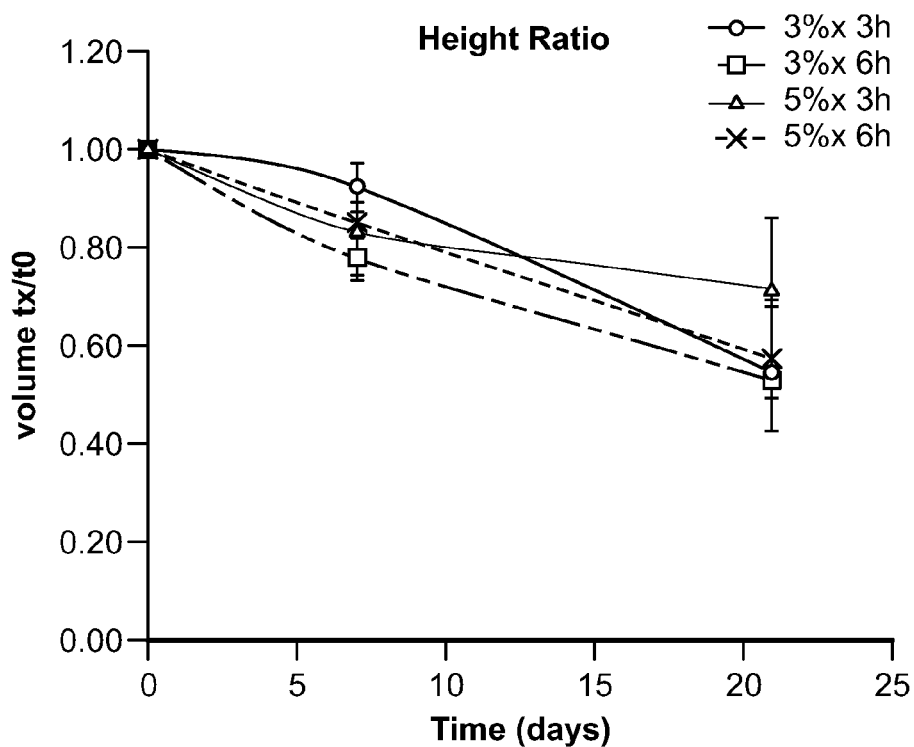
Figure 8C:
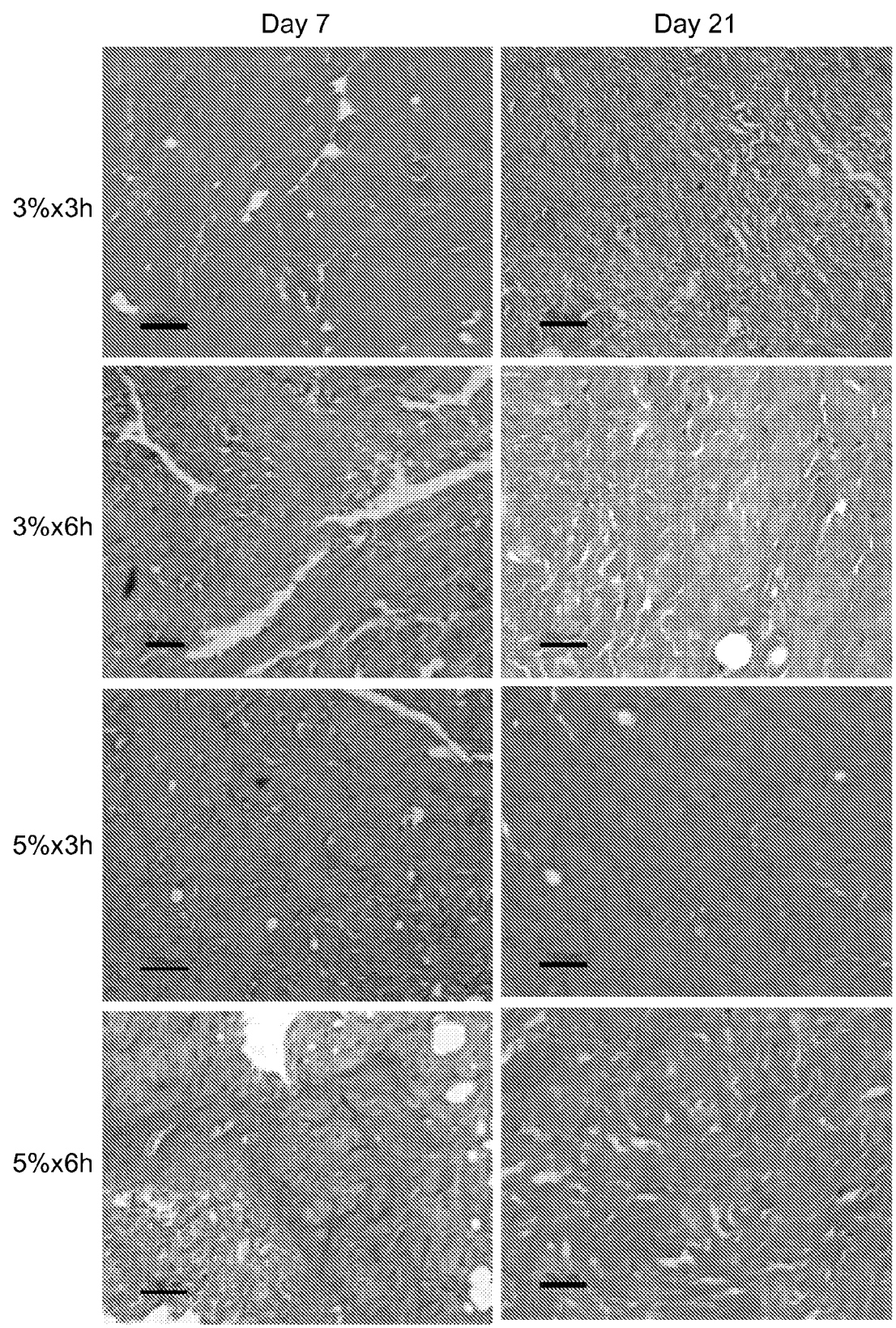

Caliper measurements indicated an initial decrease in the absolute height and volume ratio at 1 week, which appears to level off by 3 weeks (FIGS. 8A-B). The histological appearance of the tissue at harvest time demonstrates far greater tissue density than its appearance pre-implant, indicating that though some initial degradation may account for the decrease in the volume of the implant over time, tissue compaction underneath the muscular skin of a rat may also be contributing to the initial decrease in volume.

Observations using PhAT prepared using PAA/TX-100/ DNAse I were similar to those prepared without DNAse I. Further, cross-linking of PhAT provided a more protease resistant material that was still biocompatible.

Removal of a sufficient amount of the cellular lipid debris, which has the potential to induce inflammation and toxicity, is an important challenge in processing adipose tissue. In our study, a concentration of peracetic acid (PAA) of at least 3% w/v resulted in a significant reduction in lipids. Characterization of the resulting PhAT demonstrated a concentrating effect on the matrix components, including proteins, collagen, and glycosaminoglycans (GAGs). It is the retention of these ECM components that maintain the instructional capacity of this material. PhAT prepared with 3% PAA was also able to support cellular adhesion when seeded with MSCs, indicating that the processing method does not significantly alter its structural and biological properties.

We believe this material has important potential for clinical translation and therefore investigated its in vivo biocompatibility. There was no evidence of rejection or toxicity as a minimal inflammatory response was seen and there was no evidence of tissue necrosis. Nonetheless, cells were seen in the center of the implant material, demonstrating the potential for tissue integration in the subcutaneous space in the rat, where there was minimal fat pad available.

Volume persistence is another concern in clinical use of this material. Caliper measurement studies indicated an initial dropping in volume, however, when the material was harvested, both grossly and histologically, a far more dense material was retrieved. Without being bound by mechanism, we believe compaction of the material, in addition to some degradation, can explain the persistence plot. As a biological material, we expect some degradation to occur as the PhAT is being incorporated and remodeled, however, tissue that becomes fully incorporated will have long-lasting persistence.

Decellularized tissue has made an important contribution to reconstructive surgery. Used clinically, acellular dermis and bone have shown to facilitate tissue integration and restoration. Though others, such as Flynn et al., have decellularized various tissue, such as placenta, with the aim of creating a scaffold for adipogenesis, this technique has yet to be applied directly to adipose tissue. As our understanding of the role of the extracellular matrix in tissue production expands, it is clear that matrix components do not just serve a structural role in tissue, but actively participate in the instructional aspect of cellular proliferation, migration, and differentiation, and ultimately, tissue formation. Much has recently been elucidated about the role of the various ECM degradation components in influencing cell migration and proliferation. In view of the ECM as serving this instructional role, we looked to the original tissue, adipose tissue itself, believing it to be uniquely suited to provide instructions for adipogenesis. In this study we demonstrate that adipose tissue can be successfully decellularized and serve as a potential material for soft tissue reconstruction.

Removal of a sufficient amount of the cellular lipid debris, which has the potential to induce inflammation and toxicity, is an important challenge in processing adipose tissue. In our study, a concentration of peracetic acid (PAA) of at least 3% w/v resulted in a significant reduction in lipids. Continued optimization of the mechanical processing has proven that greater lipid extraction can be done at a lower concentration of PAA. Characterization of the resulting PhAT demonstrated a concentrating effect on the matrix components, including proteins, collagen, and GAGs. It is the retention of these ECM components that maintain the instructional capacity of this material. PhAT prepared with 3% PAA had rheological properties in the same order of magnitude as unprocessed adipose tissue and was also able to support cellular adhesion when seeded with MSCs, indicating that the processing method does not significantly alter its structural and biological properties.

We believe this material has important potential for clinical translation and therefore investigated its in vivo biocompatibility. There was no evidence of rejection or toxicity as a minimal inflammatory response was seen and there was no evidence of tissue necrosis. These studies used a small implant size, 200 µl. Nonetheless, fibroblastic-like cells were seen in the center of the implant material, demonstrating the potential for tissue integration in the subcutaneous space in the rat, where there was minimal fat pad available. Others have show that when Matrigel® is implanted contiguous to adipose tissue, it has the potential to be adipogenic in vivo.[7] Future studies with implantation near the epididymal fat pad in a rat would explore PhAT's adipogenic potential when in contact with an adipose environment, as one would expect in the breast, for example. Furthermore, it is the host cells that are being stimulated to become adipocytes when exposed to matrigel. Studies have identified that it is the basement membrane components, specifically, collagen type IV and laminin that are responsible for the adipogenic potential. As adipose tissue is a highly vascularized tissue, the basement membrane proteins of the many microvessels found in adipose tissue will likely confer on it this adipogenic potential.

The invention provides for the use of injectable biomaterials, including breast augmentation, to which the biocompatible biomaterials of the invention are uniquely suited. The use of the biomaterials of the invention provide solutions to problems with prior fillers and allow for elimination of scar, reduced surgical and anesthesia time, eliminations of foreign body reaction to a synthetic breast implant, as well as providing a more natural feel, for example in breast reconstruction.

Methods to prolong the persistence of transferred autologous fat have been intensely pursued. Biomaterials have been used for this purpose in numerous tissue types. A major limitation in the application of biomaterials to lipid tissue is the phase separation when mixing hydrophilic biomaterials with lipids. Compositions and methods provided herein overcome these limitations through the use of a surfactant, thus facilitating the application of a variety of biomaterials to lipid tissue. Alternatively, the compositions of the invention provide a scaffold for fat cells without requiring the incorporation of the fat cells into the biomaterial.

The use of currently available commercial fillers is limited by both volume and longevity. Although autologous fat provides greater volume, its use is limited by its low graft survival rate, due in part to cellular necrosis. By developing compositions and methods for combining biomaterial based scaffolds, such as hyaluronic acid or hydrogels to fat, both of these problems are simultaneously addressed. The combination of fat and biomaterials such as biocompatible polymers provides an immediately greater volume of biomaterial. Secondly, the compositions of the invention utilize the dual nature of hyaluronic acid and other biomaterials, behaving as both a scaffold in addition to a volume enhancing biomaterial, therefore providing a network that allows cellular attachment, vascular ingrowth, and interaction with growth factors, which addresses the problem of cellular death believed to be responsible for poor fat graft survival. The PAT of the instant invention can be combined with fresh autologous lipoaspirate or other cell containing mixtures, with natural biomaterials, such as hyaluronic acid, chondroitin sulfate, collagen, elastin, or laminin, for example, or other biomaterials such as biocompatible polymers and adhesives for use for any of a number of applications.

The invention provides a surfactant system to allow the combination of various hydrophilic scaffolds, including commercially available hyaluronic acid and hydrogels, to hydrophobic adipose tissue to be used in fat transfer. Currently, lipoaspirate is injected in desired locations unprocessed. Through the use of a surfactant system provided herein, it is now possible to appropriately emulsify hydrophilic biomaterials with adipose tissue, prior to re-injection of lipoaspirate. This has the desired effect of enhancing the survival of the autologous fat grafts by providing mature and pre-adipocytes with a scaffold to which to adhere. In addition, the use of a biomaterial scaffold as the delivery agent enables the incorporation of various growth promoting factors to stimulate adipogenesis thereby promoting graft survival, another novelty to current fat transfer techniques Modifications of the invention include the use of various surfactants, provided herein, particularly for use with the cellular biomaterial.

Further modifications include the use of various biomaterials, including Poly(ethylene-glycol) diacrylate (PEG-A), hyaluronic acid (HA) available as commercial fillers including but not limited to Restylane, Juvaderm, Captique, Teoxyl.

The invention further provides for the incorporation of Mesenchymal Stem Cells (MSCs), Embryonic Stem Cells (ES), Adipose Tissue Derived Stem Cells (ASCs), fibroblasts as well as other cell types into the biomaterial encapsulated lipoaspirate. Further variations include scaffold modifications to include peptides, hormones, growth factors, vitamins, receptors, drugs, and other regulatory factors. Clinical application includes facial reconstruction, breast reconstruction, injection laryngoplasty, treating HIV protease-induced lipoatrophy, cosmetic surgery including breast, buttock, calf, pectoralis, lip, and cheek augmentation, reversing wrinkles and filling in defects including scars, traumatic injury, congenital defects, surgical scars, burns, and defects from tumor resection.

Crosslinkable Hydrophillic Polymers

Suitable hydrophilic polymers include synthetic polymers such as poly(ethylene glycol), poly(ethylene oxide), partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll™, polysucrose, hyaluronic acid, dextran, heparan sulfate, chondroitin sulfate, heparin, or alginate, and proteins such as gelatin, collagen, albumin, or ovalbumin or copolymers or blends thereof. As used herein, "celluloses" includes cellulose and derivatives of the types described above; "dextran" includes dextran and similar derivatives thereof.

Examples of materials which can be used to form a hydrogel include modified alginates. Alginate is a carbohydrate polymer isolated from seaweed, which can be crosslinked to form a hydrogel by exposure to a divalent cation such as calcium, as described, for example in WO 94/25080, the disclosure of which is incorporated herein by reference. Alginate is ionically crosslinked in the presence of divalent cations, in water, at room temperature, to form a hydrogel matrix. Modified alginate derivatives may be synthesized which have an improved ability to form hydrogels. The use of alginate as the starting material is advantageous because it is available from more than one source, and is available in good purity and characterization. As used herein, the term "modified alginates" refers to chemically modified alginates with modified hydrogel properties. Naturally occurring alginate may be chemically modified to produce alginate polymer derivatives that degrade more quickly. For example, alginate may be chemically cleaved to produce smaller blocks of gellable oligosaccharide blocks and a linear copolymer may be formed with another preselected moiety, e.g. lactic acid or epsilon-caprolactone. The resulting polymer includes alginate blocks which permit ionically catalyzed gelling, and oligoester blocks which produce more rapid degradation depending on the synthetic design. Alternatively, alginate polymers may be used wherein the ratio of mannuronic acid to guluronic acid does not produce a film gel, which are derivatized with hydrophobic, water-labile chains, e.g., oligomers of epsilon-caprolactone. The hydrophobic interactions induce gelation, until they degrade in the body.

Additionally, polysaccharides which gel by exposure to monovalent cations, including bacterial polysaccharides, such as gellan gum, and plant polysaccharides, such as carrageenans, may be crosslinked to form a hydrogel using methods analogous to those available for the crosslinking of alginates described above. Polysaccharides which gel in the presence of monovalent cations form hydrogels upon exposure, for example, to a solution comprising physiological levels of sodium. Hydrogel precursor solutions also may be osmotically adjusted with a non-ion, such as mannitol, and then injected to form a gel.

Polysaccharides that are very viscous liquids or are thixotropic, and form a gel over time by the slow evolution of structure, are also useful. For example, hyaluronic acid, which forms an injectable gel with a consistency like a hair gel, may be utilized. Modified hyaluronic acid derivatives are particularly useful. As used herein, the term "hyaluronic acids" refers to natural and chemically modified hyaluronic acids. Modified hyaluronic acids may be designed and synthesized with preselected chemical modifications to adjust the rate and degree of crosslinking and biodegradation. For example, modified hyaluronic acids may be designed and synthesized which are esterified with a relatively hydrophobic group such as propionic acid or benzylic acid to render the polymer more hydrophobic and gel-forming, or which are grafted with amines to promote electrostatic self-assembly. Modified hyaluronic acids thus may be synthesized which are injectable, in that they flow under stress, but maintain a gel-like structure when not under stress. Hyaluronic acid and hyaluronic derivatives are available from Genzyme, Cambridge, Mass. and Fidia, Italy.

Other polymeric hydrogel precursors include polyethylene oxide-polypropylene glycol block copolymers such as Pluronics™ or Tetronics™, which are crosslinked by hydrogen bonding and/or by a temperature change, as described in Steinleitner et al., Obstetrics & Gynecology, vol. 77, pp. 48-52 (1991); and Steinleitner et al., Fertility and Sterility, vol. 57, pp. 305-308 (1992). Other materials which may be utilized include proteins such as fibrin, collagen and gelatin. Polymer mixtures also may be utilized. For example, a mixture of polyethylene oxide and polyacrylic acid which gels by hydrogen bonding upon mixing may be utilized. In one embodiment, a mixture of a 5% w/w solution of polyacrylic acid with a 5% w/w polyethylene oxide (polyethylene glycol, polyoxyethylene) 100,000 can be combined to form a gel over the course of time, e.g., as quickly as within a few seconds.

Charged Crosslinkable Polymer Solutions

Water soluble polymers with charged side groups may be crosslinked by reacting the polymer with an aqueous solution containing ions of the opposite charge, either cations if the polymer has acidic side groups or anions if the polymer has basic side groups. Examples of cations for cross-linking of the polymers with acidic side groups to form a hydrogel are monovalent cations such as sodium, divalent cations such as calcium, and multivalent cations such as copper, calcium, aluminum, magnesium, strontium, barium, and tin, and di-, tri- or tetra-functional organic cations such as alkylammonium salts. Aqueous solutions of the salts of these cations are added to the polymers to form soft, highly swollen hydrogels and membranes. The higher the concentration of cation, or the higher the valence, the greater the degree of cross-linking of the polymer. Additionally, the polymers may be crosslinked enzymatically, e.g., fibrin with thrombin.

Suitable ionically crosslinkable groups include phenols, amines, imines, amides, carboxylic acids, sulfonic acids and phosphate groups. Negatively charged groups, such as carboxylate, sulfonate and phosphate ions, can be crosslinked with cations such as calcium ions. The crosslinking of alginate with calcium ions is an example of this type of ionic crosslinking. Positively charged groups, such as ammonium ions, can be crosslinked with negatively charged ions such as carboxylate, sulfonate and phosphate ions. Preferably, the negatively charged ions contain more than one carboxylate, sulfonate or phosphate group.

The preferred anions for cross-linking of the polymers to form a hydrogel are monovalent, divalent or trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine); examples of synthetic polyamines are: polyethyleneimine, poly(vinylamine), and poly(allyl amine). There are also natural polycations such as the polysaccharide, chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups. These polymers can be modified to contain active species polymerizable groups and/or ionically cross-linkable groups. Methods for modifying hydrophilic polymers to include these groups are well known to those of skill in the art.

The polymers may be intrinsically biodegradable, but are preferably of low biodegradability (for predictability of dissolution) but of sufficiently low molecular weight to allow excretion. The maximum molecular weight to allow excretion in human beings (or other species in which use is intended) will vary with polymer type, but will often be about 20,000 Daltons or below. Usable, but less preferable for general use because of intrinsic biodegradability, are water-soluble natural polymers and synthetic equivalents or derivatives, including polypeptides, polynucleotides, and degradable polysaccharides.

The polymers can be a single block with a molecular weight of at least 600, preferably 2000 or more, and more preferably at least 3000. Alternatively, the polymers can include can be two or more water-soluble blocks which are joined by other groups. Such joining groups can include biodegradable linkages, polymerizable linkages, or both. For example, an unsaturated dicarboxylic acid, such as maleic, fumaric, or aconitic acid, can be esterified with hydrophilic polymers containing hydroxy groups, such as polyethylene glycols, or amidated with hydrophilic polymers containing amine groups, such as poloxamines.

Covalently Crosslinkable Polymer Solutions Covalently crosslinkable hydrogel precursors also are useful. For example, a water soluble polyamine, such as chitosan, can be cross-linked with a water soluble diisothiocyanate, such as polyethylene glycol diisothiocyanate. The isothiocyanates will react with the amines to form a chemically crosslinked gel. Aldehyde reactions with amines, e.g., with polyethylene glycol dialdehyde also may be utilized. A hydroxylated water soluble polymer also may be utilized.

Alternatively, polymers may be utilized which include substituents which are crosslinked by a radical reaction upon contact with a radical initiator. For example, polymers including ethylenically unsaturated groups which can be photochemically crosslinked may be utilized, as disclosed in WO 93/17669, the disclosure of which is incorporated herein by reference. In this embodiment, water soluble macromers that include at least one water soluble region, a biodegradable region, and at least two free radical-polymerizable regions, are provided. The macromers are polymerized by exposure of the polymerizable regions to free radicals generated, for example, by photosensitive chemicals and or light. Examples of these macromers are PEG-oligolactyl-acrylates, wherein the acrylate groups are polymerized using radical initiating systems, such as an eosin dye, or by brief exposure to ultraviolet or visible light. Additionally, water soluble polymers which include cinnamoyl groups which may be photochemically crosslinked may be utilized, as disclosed in Matsuda et al., ASAIO Trans., vol. 38, pp. 154-157 (1992).

The term "active species polymerizable group" is defined as a reactive functional group that has the capacity to form additional covalent bonds resulting in polymer interlinking upon exposure to active species. Active species include free radicals, cations, and anions. Suitable free radical polymerizable groups include ethylenically unsaturated groups (i.e., vinyl groups) such as vinyl ethers, allyl groups, unsaturated monocarboxylic acids, unsaturated dicarboxylic acids, and unsaturated tricarboxylic acids. Unsaturated monocarboxylic acids include acrylic acid, methacrylic acid and crotonic acid. Unsaturated dicarboxylic acids include maleic, fumaric, itaconic, mesaconic or citraconic acid. In one embodiment, the active species polymerizable groups are preferably located at one or more ends of the hydrophilic polymer. In another embodiment, the active species polymerizable groups are located within a block copolymer with one or more hydrophilic polymers forming the individual blocks. The preferred polymerizable groups are acrylates, diacrylates, oligoacrylates, dimethacrylates, oligomethacrylates, and other biologically acceptable photopolymerizable groups. Acrylates are the most preferred active species polymerizable group.

In general, the polymers are at least partially soluble in aqueous solutions, such as water, buffered salt solutions, or aqueous alcohol solutions. Methods for the synthesis of the other polymers described above are known to those skilled in the art. See, for example Concise Encyclopedia of Polymer Science and Polymeric Amines and Ammonium Salts, E. Goethals, editor (Pergamen Press, Elmsford, N.Y. 1980). Many polymers, such as poly(acrylic acid), are commercially available.

Naturally occurring and synthetic polymers may be modified using chemical reactions available in the art and described, for example, in March, "Advanced Organic Chemistry," 4th Edition, 1992, Wiley-Interscience Publication, New York. Such methods may be used to, for example, introduce acrylate groups as described herein.

Preferably, the hydrophilic polymers that include active species or crosslinkable groups include at least 1.02 polymerizable or crosslinkable groups on average, and, more preferably, each includes two or more polymerizable or crosslinkable groups on average. Because each polymerizable group will polymerize into a chain, crosslinked hydrogels can be produced using only slightly more than one reactive group per polymer (i.e., about 1.02 polymerizable groups on average). However, higher percentages are preferable, and excellent gels can be obtained in polymer mixtures in which most or all of the molecules have two or more reactive double bonds. Poloxamines, an example of a hydrophilic polymer, have four arms and thus may readily be modified to include four polymerizable groups.

Methods of Implantation

In a preferred embodiment, the compositions of the invention are prepared and injected directly into a site where it is desired to implant the material. If a cross-linking agent is to be used, the material is preferably injected prior to crosslinking of the polymer to form the hydrogel. In a preferred method, the crosslinking occurs sufficiently rapidly such that there is no substantial migration of the biomaterial away from the site of injection. In particular embodiments, it may be advantageous to deliver the biomaterial by multiple injections, either at multiple sites or at periodic time intervals, intervals of minutes, hours, days, weeks, or longer. Periodic implantation may be required to allow the skin to stretch to accommodate the biomaterial (e.g., during breast reconstruction after mastectomy).

The site, or sites, where the biomaterials of the invention are to be injected is determined based on individual need, as is the requisite number of cells when the biomaterial contains cells. One can apply an external mold to shape the injected solution. Additionally, by controlling the rate of polymerization, it is possible to mold the biomaterial injected implant like one would mold clay. Alternatively, the mixture can be injected into a mold, the biomaterial allowed to harden, then the material implanted.

The composition can be injected via a syringe and needle or any appropriately designed injection apparatus or minimally invasive implantation device directly into a specific area wherever a bulking agent is desired, i.e., a soft tissue deformity such as that seen post-operatively or with areas of muscle atrophy due to congenital or acquired diseases or secondary to trauma, burns, and the like. An example of this would be the injection of the composition in the breast area after mastectomy or in the upper torso of a patient with muscular atrophy secondary to nerve damage.

The suspension can also be injected percutaneously by direct palpation, such as by placing a needle inside the vas deferens and occluding the same with the injected bulking substance, thus rendering the patient infertile. The suspension can also be injected through a catheter or needle with fluoroscopic, sonographic, computed tomography, magnetic resonance imaging or other type of radiologic guidance. This would allow for placement or injection of this substance either by vascular access or percutaneous access to specific organs or other tissue regions in the body, wherever a bulking agent would be required. Further, this substance could be injected through a laparoscope or thoracoscope to any intraperitoneal or extraperitoneal or thoracic organ.

Optionally, various additives can be included in the hydrogel solution such as 100 U/ml of penicillin and 100 µg/ml streptomycin to inhibit microbacterial contamination. However, these are not the only bioactive additives that can be included in the hydrogel solution. For example, the bioactive additives could include, singly or in combination, growth factors, cell differentiation factors, other cellular mediators, nutrients, antibiotics, anti-inflammatories, and other pharmaceuticals. Although not limiting, some suitable cellular growth factors, depending upon the cell type, if any, to be encapsulated in either the hydrogel of the same or adjacent hydrogel layer, include heparin binding growth factor (HBGF), transforming growth factor (TGF$\alpha$ or TGF$\beta$), alpha fibroblastic growth factor (FGF), epidermal growth factor (EGF), vascular endothelium growth factor (VEGF), various angiogenic factors, growth factors, nerve growth factor (NGF), and muscle morphologic growth factor.

In addition, the hydrogel solution optionally includes a suitable non-toxic polymerization initiator, mixed thoroughly to make a final concentration of 0.05% w/v. When PEGDA or PEODA are selected as the polymers, the polymerization initiator is preferably added and selected to be the photoinitiator Igracure™ 2959 (commercially available from Ciba Specialty Chemicals Corp., Tarrytown, N.Y.), although other suitable photoinitiators can be used.

While photopolymerizable PEGDA and PEODA are among the preferred polymers for making hydrogels in accordance with the present invention, other suitable hydrophilic polymers can be used. Suitable hydrophilic polymers include synthetic polymers such as partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll® polysucrose, hyaluronic acid, dextran, heparan sulfate, chondroitin sulfate, heparin, or alginate, and proteins such as gelatin, collagen, albumin, or ovalbumin or copolymers or blends thereof. As used herein, "celluloses" includes cellulose and derivatives of the types described above; "dextran" includes dextran and similar derivatives thereof. This list of photopolymerizable mixtures is meant to be illustrative and not exhaustive. For example, other photopolymerizable mixtures suitable for application in the present invention are described in U.S. Pat. No. 6,224,893 B1, which is incorporated herein by reference.

While a preferred photoinitiator is Igracure™ 2959, various other photoinitiators can be used instead. For example, HPK, which is commercially available from Polysciences, is another suitable photoinitiator. In addition, various dyes and an amine catalyst are known to form an active species when exposed to external radiation. Specifically, light absorption by the dye causes the dye to assume a triplet state, which subsequently reacts with the amine to form the active species that initiates polymerization. Typically, polymerization can be initiated by irradiation with light at a wavelength of between about 200-700 nm, most preferably in the long wavelength ultraviolet range or visible range, 320 nm or higher, and most preferably between about 365 and 514 nm.

Numerous dyes can be used for photopolymerization, and these include erythrosin, phloxime, rose bengal, thonine, camphorquinone, ethyl eosin, eosin, methylene blue, riboflavin, 2,2-dimethyl-2-phenylacetophenone, 2-methoxy-2-phenylacetophenone, 2,2-dimethoxy-2-phenyl acetophenone, other acetophenone derivatives, and camphorquinone. Suitable cocatalysts include amines such as N-methyl diethanolamine, N,N-dimethyl benzylamine, triethanol amine, triethylamine, dibenzyl amine, N-benzylethanolamine, N-isopropyl benzylamine. Triethanolamine is a preferred co-catalyst with one of these dyes. Photopolymerization of these polymer solutions is based on the knowledge that combinations of polymers and photoinitiators (in a concentration not toxic to the cells, less than 0.1% by weight, more preferably between 0.05 and 0.01% by weight percent initiator) will crosslink upon exposure to light equivalent to between one and 3 mWatts/cm$^2$.

While photopolymers are preferred for making the hydrogels, because it is convenient to control polymerization using external radiation supplied through a surgical scope, the present invention can be practiced using other polymer materials and polymerization initiators. Examples of other materials which can be used to form a hydrogel include (a) modified alginates, (b) polysaccharides (e.g. gellan gum and carrageenans) which gel by exposure to monovalent cations, (c) polysaccharides (e.g., hyaluronic acid) that are very viscous liquids or are thiotropic and form a gel over time by the slow evolution of structure, and (d) polymeric hydrogel precursors (e.g., polyethylene oxide-polypropylene glycol block copolymers and proteins). U.S. Pat. No. 6,224,893 B1 provides a detailed description of the various polymers, and the chemical properties of such polymers, that are suitable for making hydrogels in accordance with the present invention, and this patent is incorporated herein by reference in its entirety.

Polymerizable agents for use in the instant invention may comprise monomers, macromers, oligomers, polymers, or a mixture thereof. The polymer compositions can consist solely of covalently crosslinkable polymers, or blends of covalently and ionically crosslinkable or hydrophilic polymers.

Crosslinkers of Acellular Biological Tissues

It was previously reported that acellular biological tissues can provide a natural microenvironment for host cell migration and may be used as a scaffold for tissue regeneration. To reduce antigenicity, biological tissues have to be fixed with a crosslinking agent before implantation. In a study by Liang, H.-C., et al., 2004, a cell extraction process was employed to remove the cellular components from bovine pericardia. The acellular tissues then were fixed with genipin, a cross-linker, at various known concentrations to obtain varying degrees of cross-linking. It was shown in the in vitro degradation study that after fixing with genipin, the resistance against enzymatic degradation of the acellular tissue increased significantly with increasing its crosslinking degree. In the in vivo subcutaneous study, it was found that cells (inflammatory cells, fibroblasts, endothelial cells, and red blood cells) were able to infiltrate into acellular tissues. Generally, the depth of cell infiltration into the acellular tissue decreased with increasing its crosslinking degree. Infiltration of inflammatory cells was accompanied by degradation of the acellular tissue. Due to early degradation, no tissue regeneration was observed within fresh (without crosslinking) and the 30%-degree-crosslinking acellular tissues. This is because the scaffolds provided by these two samples were already completely degraded before the infiltrated cells began to secrete their own extracellular matrix. In contrast, tissue regeneration (fibroblasts, neo-collagen fibrils, and neo-capillaries) was observed for the 60%- and 95%-degree-cross-linking acellular tissues by the histological examination, immunohistological staining, transmission electron microscopy, and denaturation temperature measurement. The 95%-degree-cross-linking acellular tissue was more resistant against enzymatic degradation than its 60%-degree-crosslinking counterpart. Consequently, tissue regeneration was limited in the outer layer of the 95%-degree-crosslinking acellular tissue throughout the entire course of the study (1-year postoperatively), while tissue regeneration was observed within the entire sample for the 60%-degree-crosslinking acellular tissue. Liang, H.-C., et al., concluded that the crosslinking degree determines the degradation rate of the acellular tissue and its tissue regeneration pattern. These data demonstrate that the rate of degradation and the amount of cellular infiltration can be controlled by the amount of cross-linking of the processed adipose tissue.

Methods of cross-linking of acellular tissues are known in the art. For example, acellular tissues can be fixed in an aqueous genipin (Challenge Bioproducts, Taichung, Taiwan) solution at various known concentrations buffered with phosphate buffered saline (PBS, 0.1 m, pH 7.4, Sigma Chemical Co.) at 37° C. for 3 days. The degree of cross-linking, can be determined by the ninhydrin assay (Stryer, Biochemistry, 3$^{rd}$. ed, New York, Freeman, 1988, 50-55, incorporated herein by reference) or using a commercially available kit such as those offered by AnaSpec. The amount of cross-linking is defined as the percentage of free amino groups in acellular tissues reacted with a cross-linking agent such as genipin subsequent to fixation. The denaturation temperature of each studied group (corresponds to the denaturation of collagen) can be measured, for example, in a Perkin-Elmer differential scanning calorimeter (Model DSC 7, Norwalk, Conn., USA). This technique has been widely used in studying the thermal transition of collagenous biomaterials. A heating rate was 5° C./min can be used. Typically, the temperature scanned is in an approximate range of (Td225° C.)<T<(Td+10° C.); where Td is the relevant denaturation temperature. The use of a sealed aluminum pan is recommended for volatile compounds.

The specific amount of cross-linker, the cross-linking time, and the cross-linking temperature can be varied depending on the specific cross-linker or cross-linkers used, and on the desired level of cross-linking depending on the final use of the processed adipose tissue. In certain embodiments, the processed adipose tissue has 40%-degree cross-linking to 95%-degree cross-linking. In certain embodiments, the processed adipose tissue has 50%-degree cross-linking to 90%-degree cross-linking. In certain embodiments, the processed adipose tissue has 60%-degree cross-linking to 90%-degree cross-linking. In certain embodiments, the processed adipose tissue has 60%-degree cross-linking to 80%-degree cross-linking. In certain embodiments, the processed adipose tissue has 50%-degree cross-linking to 75%-degree cross-linking. Cross-linkers for use with biological tissue derived material such as the processed adipose tissue of the instant invention include, but are not limited to, carbodiimide (EDC), hexamethylene diisocyanate (HMDC), gluteraldehyde, proanthocyanidin, ribose, threose, and lysyl oxidase, carbodiimide, polyepoxy ethers, divinyl sulfone (DVS), genipin, polyaldehyde and diphenylphosphoryl azide (DPPA), genipin, epoxy compounds, dialdehyde starch, glutaraldehyde, formaldehyde, dimethyl suberimidate, carbodiimides, succinimidyls, diisocyanates, and acyl azide Supercritical Fluid Extraction Methods for Processed Adipose Tissue Processes are known where $CO_2$ is in the compressed state during extraction, as are others where $CO_2$ is in the liquid state (Hubert et al., 1980; Wilson, 1984). This technique offers extraction yields comparable with those obtained by conventional extraction methods using organic solvents. Moreover, in contrast with organic solvents, carbon dioxide is non-toxic, non-flammable, non-corrosive, cheap, and readily available in large quantities with high purity.

Supercritical fluids technology can be used for the extraction of adipose tissue in for the preparation of processed adipose tissue herein. Supercritical fluids (SCF's) are often referred to as dense gases. Technically, an SCF is a gas existing above its critical temperature and critical pressure, as defined in the phase diagram of the pure substance. When a gas is compressed above its critical temperature, densities increase dramatically. Therefore, under a given set of conditions, an SCF may possess the density of a liquid while maintaining the diffusivity of a gas. The solvent properties of SCF's have been recognized for over 100 years but commercial applications have been slow in developing. SC—$CO_2$ is an ideal solvent because it is nontoxic, nonexplosive, cheap, readily available, and easily removed from the extracted products. Methods for extraction of lipids using SC $CO_2$ are provided, for example in U.S. Pat. No. 4,466,923 which is incorporated herein by reference.

Rheological Measurements

The processed adipose tissue materials provided herein are rheologically defined as viscoelastic materials. A viscoelastic material has viscous (liquid-like) and elastic (solid-like) characteristics when stress is applied (deformation). A viscous material, like honey, moves or flows when deformed and does not return to the original state when the deforming stress is removed. An elastic material, like rubber, moves when deformed but returns to the original state once the deforming stress is removed. For the processed adipose tissues provided herein, low- and high-stress environments are important, because they are subject to high and low stress during use. High stress is applied as the material flows out of the narrow bore needle, and the implant experiences very low stress while the material is at rest in place at the site of application in the dermis. Rheologically, the viscoelastic characteristics of the processed adipose tissue can be described by estimating the elastic modulus (G') and the viscous, or loss, modulus (G") using a rheometer in a single programmed run. The characteristics of any viscoelastic material, including processed adipose tissue, can be described according to these two values. G' and G" can be combined into an aggregate value defined as tan, wherein, tan=G'/G". A lower tan corresponds to a stiffer, more solid or elastic-like gel. The specific G', G", and tan can be modulated in the processed adipose tissue by adjusting the concentration of the processed adipose tissue material for delivery, the concentration of the cross-linker, with or without biopolymer, and other factors.

Rheological measurements can be performed using any of a number of methods known in the art. For example, small-deformation oscillation dynamic rheological measurements can be made using a Thermo Haake RS300 Rheometer (Newington, N.H.) fitted in the cone and plate geometry. Measurements can be made using a 35 mm/1° titanium cone sensor at 25° C. Oscillation measurements can be made over a frequency range, for example a frequency range of 0.628 to 198 rad/s. Percentage elasticity is calculated as percentage elasticity=(100×G')/(G'+G"). The tan, tan=G"/G', can be obtained from the dynamic modulus data at any selected frequency, for example at a frequency of 0.628 rad/s.

The Examples and figures discuss experiments and provide results from adipose tissue based implantable materials. The results shown in FIGS. 1-2 were performed using a lipoaspirate starting material. The results shown in FIGS. 3-13 were performed with solid, subcutaneous adipose tissue as a starting material. FIGS. 3-8 show results from experiments performed with less finely minced starting material treated with PAA and DNAse I, but not with TX-100. FIGS. 9-13 show results from experiments performed with more finely minced starting materials typically treated with PAA, TX-100, and DNAse I. The specific reagents used to prepare the processed human adipose tissue (PhAT) are discussed in further detail below in the examples that discuss the Figures and in the Figure Legends provided above.

Example 1—Preparation of a Cellular Biocompatible Biomaterial

A lipoaspirate was obtained using standard minimally invasive surgical techniques. Tumescent fluid was removed and the lipoaspirate was placed on ice until next step. The lipoaspirate was combined with various surfactants and scaffolds for the preparation of the biocompatible biomaterial.

1. Hyaluronic acid was emulsified with cellularized lipoaspirate in a 1:1 ratio with the addition of 5% Pluronic surfactant.

2. A 10% weight per volume PEG-DA was dissolved in a 50:50 ratio of PBS:Lipoaspirate.

FIG. 1 shows emulsification of the lipoaspirate and aqueous PEG mixture in the absence or presence of surfactant. In FIG. 1A, the far left tube contains no surfactant. Phase separation between the aqueous and lipid layers of the mixture is evident. Moving to the right, increased concentrations of surfactant were added, and improved emulsification was observed.

The HA used was a commercially available crosslinked HA which requires no cross-linker and can be molded by hand.

Figure 1B:
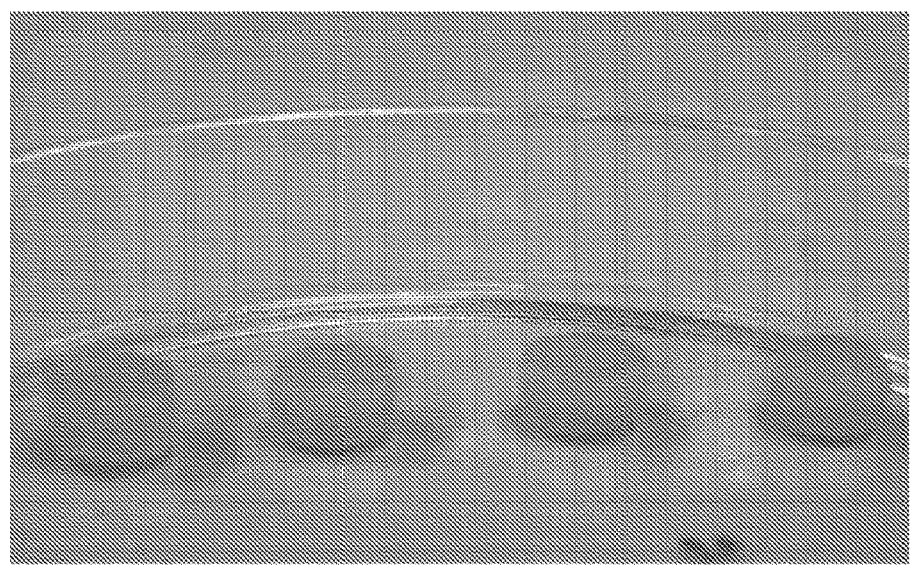

A photoinitiator was prepared and added for the polymerization of the PEG-DA mixture. Initiator solution was prepared by dissolving eosin Y disodium salt (Sigma-Aldrich CAT #45235, which absorbs most strongly in the 450-550 nm wavelength range) in PBS (GIBCO CAT #14190342) (1.375 mg/ml Eosin Y). 100 mg (10% w/v) PEODA (3.4 KD MW SunBio CAT #P2AC-3) was dissolved in 50 µl of initiator solution, 30 µl of PBS, and 20 µL of N-vinyl pyrrolidone (Sigma-Aldrich CAT #95060). Final solutions were prepared by mixing this PEODA solution with 30 µl of triethanolamine (Sigma-Aldrich #90278) and 1 ml of lipoaspirate FIG. 1B shows 10% w/v PEG dissolved in varying ratios of lipoaspirate in the presence of surfactant and HA (10%-50%). The lipoaspirate/PEG/HA can be formed into implants of the desired shape for implantation.

Figure 1C:
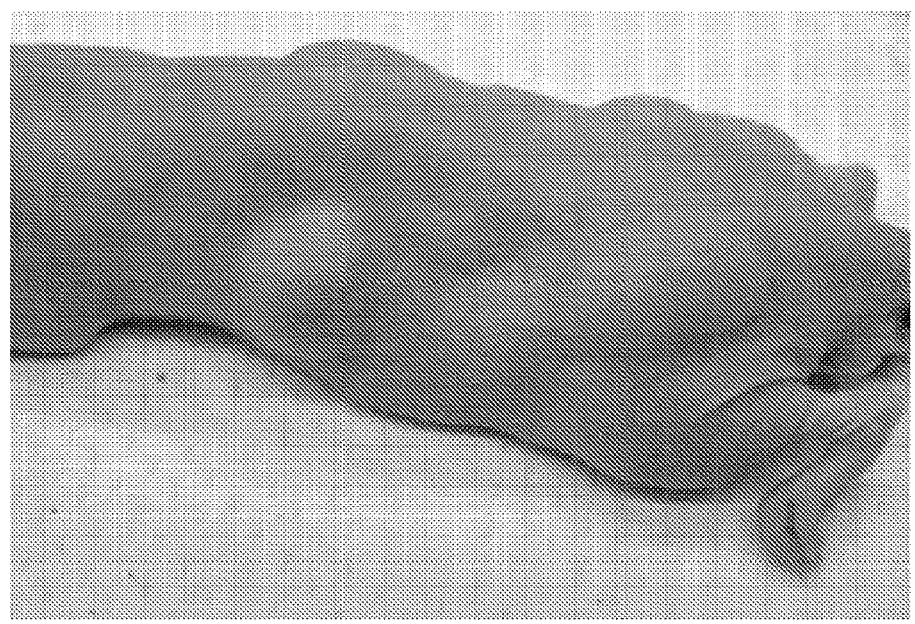

Alternatively, as shown in FIG. 1C, the lipoaspirate material can be injected and cross-linked in situ. Prior to injection, the mixtures were vortexed until mixture appeared to have a homogeneous distribution of fat. The PEG-DA/lipoaspirate mixture was injected subcutaneoulsy and a light source (e.g., light emitting diode) was applied to provide Intense Pulsed Light (IPL) in the case of hydrogel. Methods for transdermal photopolymerization are well known in the art (see, e.g., Elisseeff et al, Transdermal photopolymerization for minimally invasive implantation, *Proc. Natl. Acad. Sci, USA.* 96:3104-3107, incorporated herein by reference). FIG. 1C shows an athymic mouse after subcutaneous injections of lipoaspirate and PEG and HA. Raised bumps of cross-linked lipoaspirate can be readily seen.

To enable and predict clinical efficacy of the biocompatible biomaterials of the instant invention, a preclinical animal model has been developed and validated to predict the lifetime or persistence and tolerability of soft tissue substitutes. The persistence of subcutaneous injections of various soft tissue materials, including human adipose tissue and commercially available hyaluronic acid dermal fillers, in both athymic mice and Sprague-Dawley rats, correlates with the known clinical persistence of these materials. Persistence of the cell based biomaterials of the invention have been confirmed using MRI volumetric measurements. However, assessment can also be performed using calipers to determine height and width of the injected material.

Figure 2A:
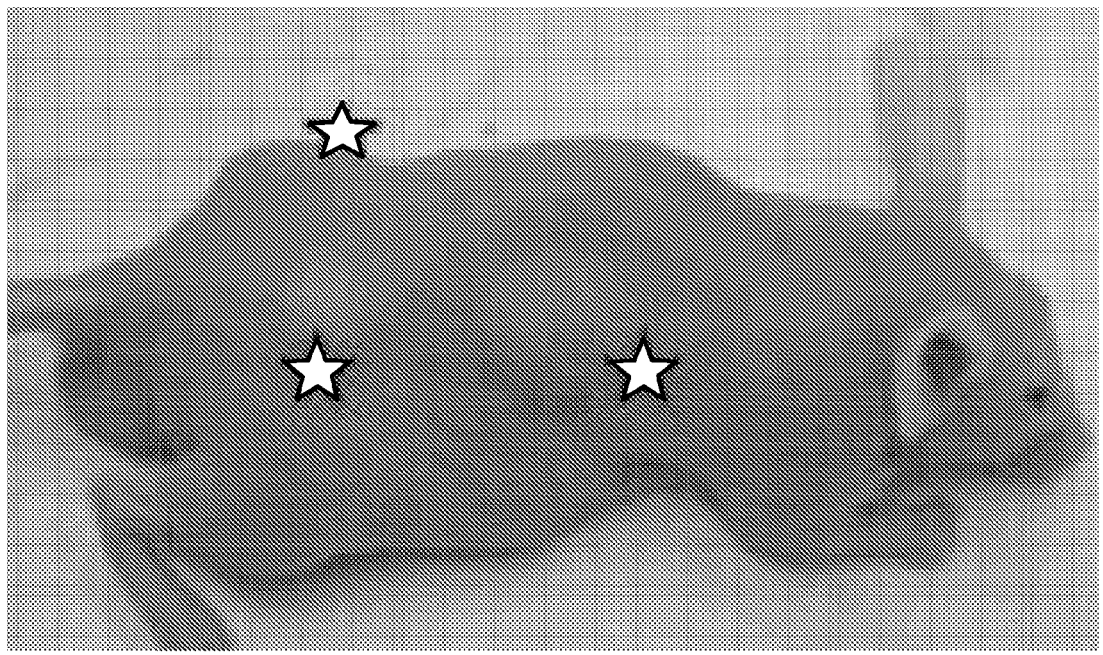
FIGS. 2A-D show A) a gross image of soft tissue implants on the dorsum of an athymic nude mouse; B) T2 MRI of a Sprague-Dawley rat with soft tissue implants, allowing for volumetric measurements; and C-D) Height and volume of C) commercially available implants and D) cellular adipose tissue either with or without hyaluronic acid are plotted over time and have been found to correlate with known clinical persistence of implanted adipose tissue and commercially available injected dermal fillers.
Figure 2B:
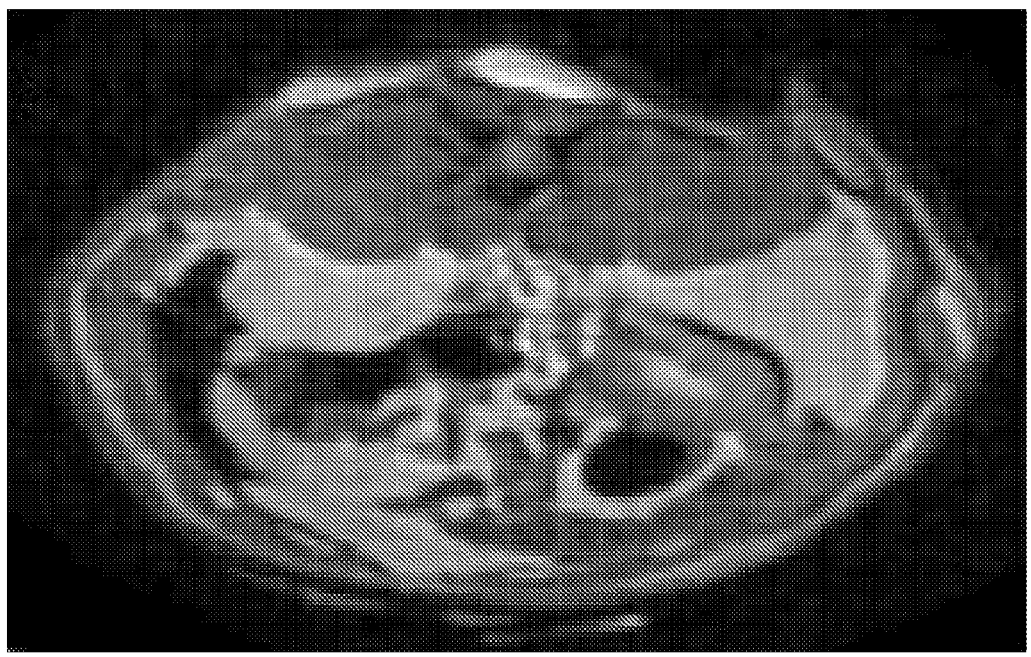
Figure 2C:
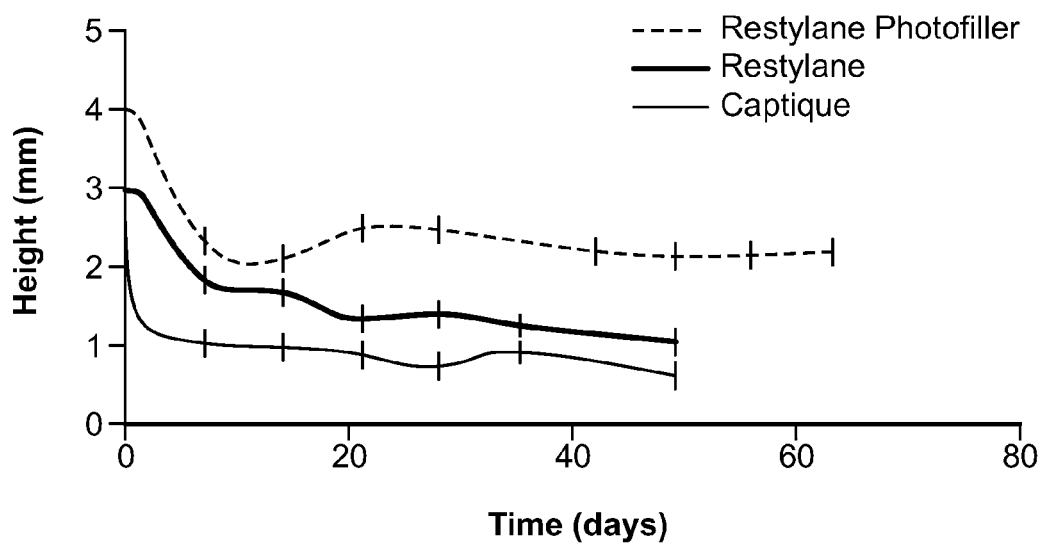
Figure 2D:
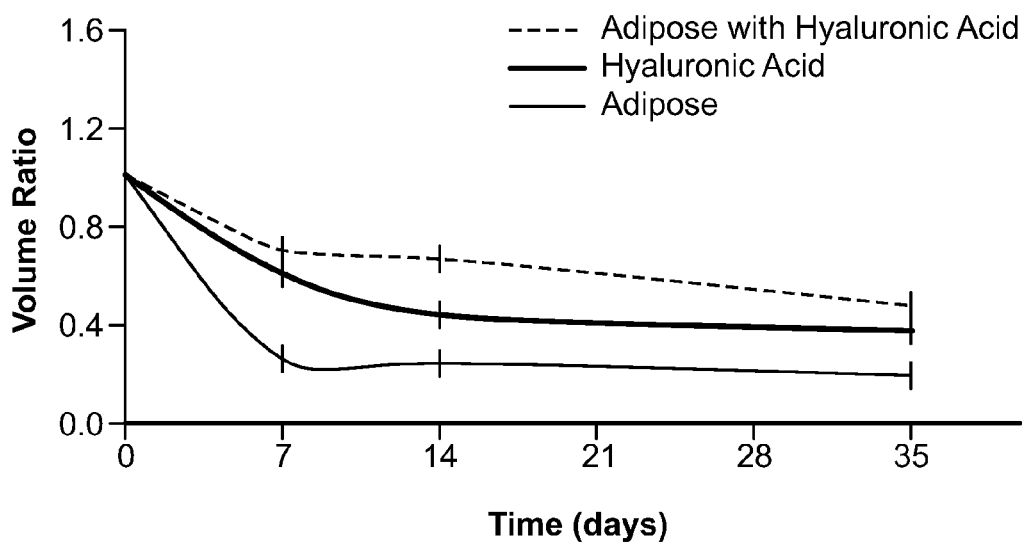

The injected lipoaspirate material, with or without HA, and HA alone, were tested for persistence in a mouse model. A similar experiment was performed using commercially available biofillers using a different measurement (height vs volume). FIG. 2A shows an athymic nude mouse injected with various biofillers. The injection sites are indicated with stars. FIG. 2B shows an image of a T2 MRI of a Sprague-Dawley rat similarly injected with soft tissue implants, allowing for volumetric measurements. Height and volume of commercially available implants, in FIG. 2C, and cellular adipose tissue, in FIG. 2D, either with or without hyaluronic acid are plotted over time. Good persistence of the lipoaspirate material is shown. Further, the persistence of the material has been found to correlate with known clinical persistence of implanted adipose tissue and commercially available injected dermal fillers. For example, at 35 days, over 50% of the volume of the adipose with HA was still present. Hyaluronic acid alone, or adipose alone were found to dissipate more rapidly Example 2—Preparation of Acellular Biomaterial/Processed Human Adipose Tissue (PhAT)

Tissue Acquisition and Processing.

Figure 3B:
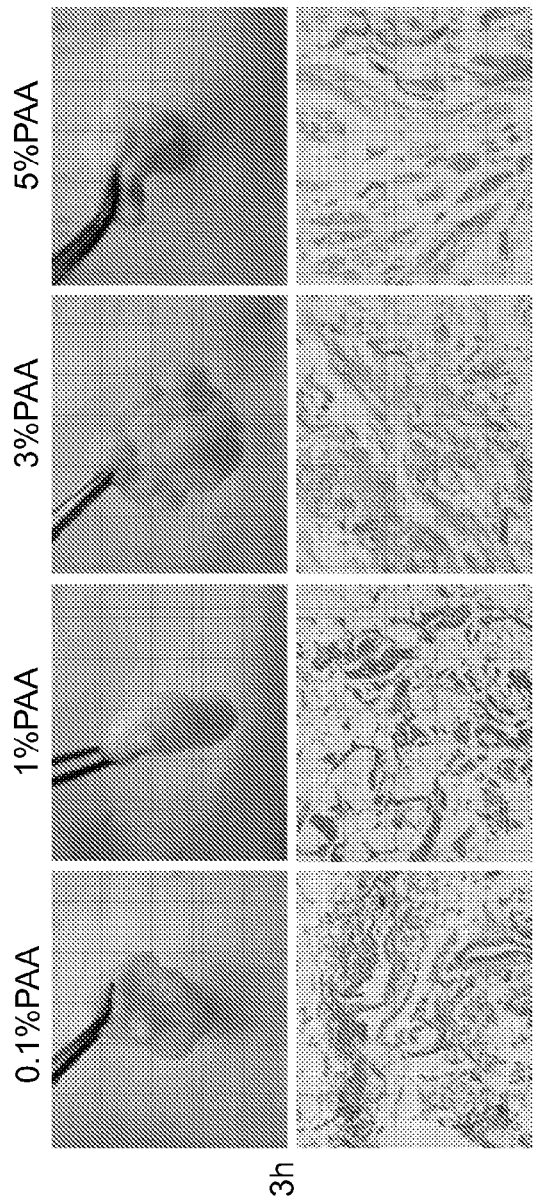
FIGS. 3A-C shows A) a sample of donor abdominoplasty skin with underlying subcutaneous adipose tissue, pre-processed. B) shows gross (top) and H&E (bottom) stained images of adipose tissue with varying (0.1%-5%) concentrations of Peracetic Acid (PAA) for 3 or 6 hours. C) shows H&E stain of pre-processed adipose tissue with dark purple (hematoxylin) stained nuclei and empty space architecture reflecting the lipid filled vacuoles. Compared to the gross image of pre-processed adipose tissue (A) a loss of characteristic yellow color is seen with increasing concentrations of PAA (B). C) shows the dark purple hematoxylin staining of nuclei and vacuolar empty spaces in pre-processed tissue, as seen in (C), is no longer present in the processed tissue (B), confirming that decellularization and the condensation of the ECM occurred during the processing method.
Figure 3A:
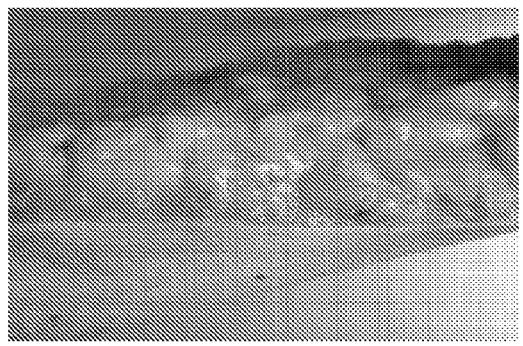
Figure 9A:
FIGS. 9A-F show the steps of adipose tissue processing using finely minced adipose tissue. A) shows an example of adipose tissue sample obtained from an abdominoplasty procedure. B) shows processed adipose tissue matrix after treatment with both 3% PAA and TX-100. C) shows a histological image of H&E stained intact adipose tissue, and D) shows a histological image of H&E stained decellularized adipose tissue showing no remnants of cellular components. Results from E) DNA quantification and F) collagen assays of tissue processed with varying peracetic acid concentrations from 0.1%-5% for three hours.
Figure 9B:
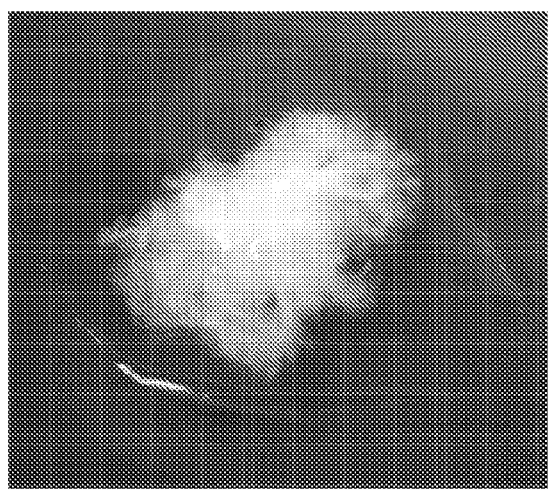
Figure 9C:
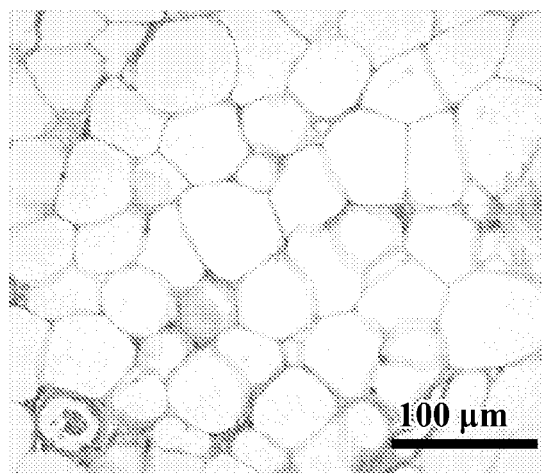
Figure 9D:
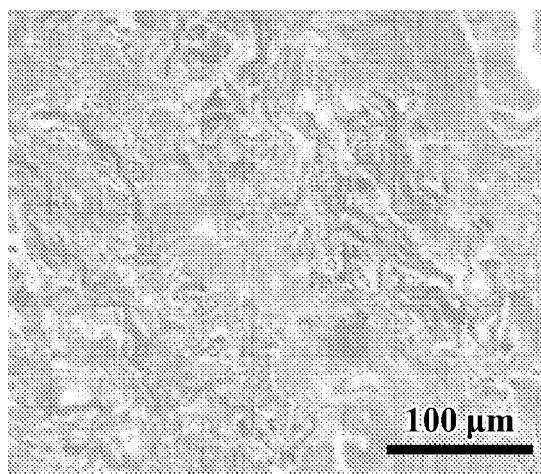

Tissue was acquired from fresh surgical and cadaveric sources with appropriate consent of the donors. A representative sample of subcutaneous fat is shown in FIGS. 3A and 9A. A representative histological section showing nuclei, lipid vacuoles, and extracellular matrix is provided in FIGS. 3C and 9C.

Subcutaneous fat was isolated from the sample by scraping. The scraped adipose tissue was homogenized in a blender. The homogenate was then placed on a strainer and washed for 5 minutes under deionized water to wash lipid and cellular debris. This was repeated three times. An equal weight of the homogenized and washed tissue was placed in 0.1%, 1%, 3%, or 5% peracetic acid for 3 or 6 hours on a shaker at 37° C. As adipocytes die, oil is released from the cells. To fully infiltrate the adipose tissue and remove the oil, the material was manually manipulated with a mortar and pestle, or homogenized in a blender or with a press between washes with PBS. As the lipid was removed, the processed adipose material changed from yellow to white (FIG. 3B).

Alternatively, the scraped adipose tissue was finely minced by forcing the material repeatedly through a die while rinsing with water to remove lipid. The minced material was transferred to a tube for solubilization using a 0.1%-5% solution of a weak acid, e.g., peracetic acid (PAA) in sterile distilled water for 3-6 hours at 37° C. with shaking to promote chemical decellularization.

The PAA treated material was washed with phosphate buffered saline (PBS) to remove debris and to return the pH to physiological pH.

In certain experiments, the PAA treated material was treated with 1% Triton® X-100 in 2 mM EDTA in sterile water overnight at 37° C. to further remove lipids. The material was rinsed repeatedly in PBS to remove detergent.

In certain experiments, the PAA treated material or the PAA/Triton® X-100 treated material (FIG. 9B) was further nuclease treated in a solution of 0.1% of DNAse I or 600 units/ml DNAse in 10 mM $MgCl_2$ at 37° C. overnight.

The processed material was rinsed repeatedly with PBS prior to storage. The processed material was stored at −20° C. in PBS with antibiotic, e.g., 1% penicillin/streptomycin or 10% Antibiotic-Antimycotic solution (A5955 Sigma-Aldrich, St. Louis, Mo.). Optionally, the material was flash frozen and lyophilized for 2-3 prior to storage at room temperature.

The processed adipose material was made into particles for injection with or without a biopolymer scaffold and cross-linking agents.

The processed adipose material was characterized using the methods provided herein. It was determined that more finely minced tissue which was also treated with Triton® X-100 resulted in greater removal of lipids and nucleic acids. However, adipose processed by either method produced a processed material that had good persistence in vivo as compared to commercially available tissue fillers, produced minimal immune response, and supported cell growth in vitro and in vivo.

Example 3—Analysis of Acellular Biocompatible Biomaterial

The acellular biocompatible biomaterial (processed human adipose tissue or PhAT) was tested using a number of assays to demonstrate that the material is acellular, lipid-free, includes intact extracellular matrix (ECM), and the appropriate dynamic stiffness. Exemplary assays used are provided. Other methods to determine if the material has the desired characteristics are known in the art.

Cell Free. Hematoxylin and eosin (H&E) staining was performed on paraffin-embedded sections of PAT prepared by at least one of the methods of the previous example to determine the presence of nuclei (cells) (compare FIGS. 7C and 9C to FIGS. 7B and 9D). No cellular material or nuclei were observed after processing with PAA and DNAse (FIG. 7B) or with PAA, TX-100, and DNAse (FIG. 9D) per the methods of the invention.

In addition, MHC class I immunostaining can be performed to evaluate the presence of antigens.

DNA Content:

To demonstrate degree of decellularization, a DNA assay was done. For fluorometric DNA assays, calf thymus DNA standards were prepared with 0-100 µg/ml DNA. Samples (100 µl) or standards were mixed with 33258 Hoechst solution (0.1 µg/ml, Molecular probes, Eugene, Oreg.) dissolved in 1×TNE buffer (10 mM Tris, 1 mM EDTA, 0.2 M NaCl, pH. 7.4). DNA content was determined with a fluorometer (Hoefer DyNA Quant 200 Florometer) using A365 nm excitation and A458 nm emission, and calculated from the calf thymus DNA standard curve.

Figure 9E:
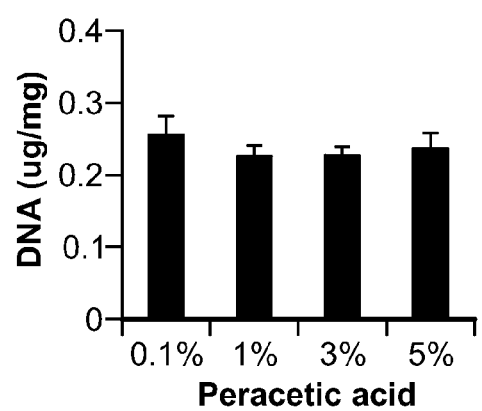

Biochemical analysis of the composition of decellularized adipose tissue showed little donor variability across the three different donors. As shown, the PAA and nuclease (FIG. 4) and the PAA, TX-100, and nuclease (FIG. 9E) treatments removed a substantial amount of the nucleic acid present in the sample. Due to the significantly reduced volume of the processed material as compared to the starting material, no comparison is made to the original material in FIG. 9. In FIG. 9, samples treated with 0.1% peracetic acid had the highest DNA content in comparison with samples from higher acid concentrations, which gave similar results despite varying the acid concentration from 1% to 5% (FIG. 9E). These results demonstrate that the PhAT of the invention removes a significant amount of nucleic acid from the tissue, with the specific concentration of PAA having less of an effect on the nucleic acid removal in the more finely minced sample that is also treated with TX-100.

Lipid Free.

Figure 3C:
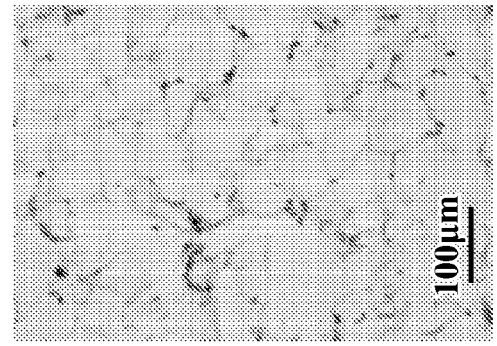
Figure 4:
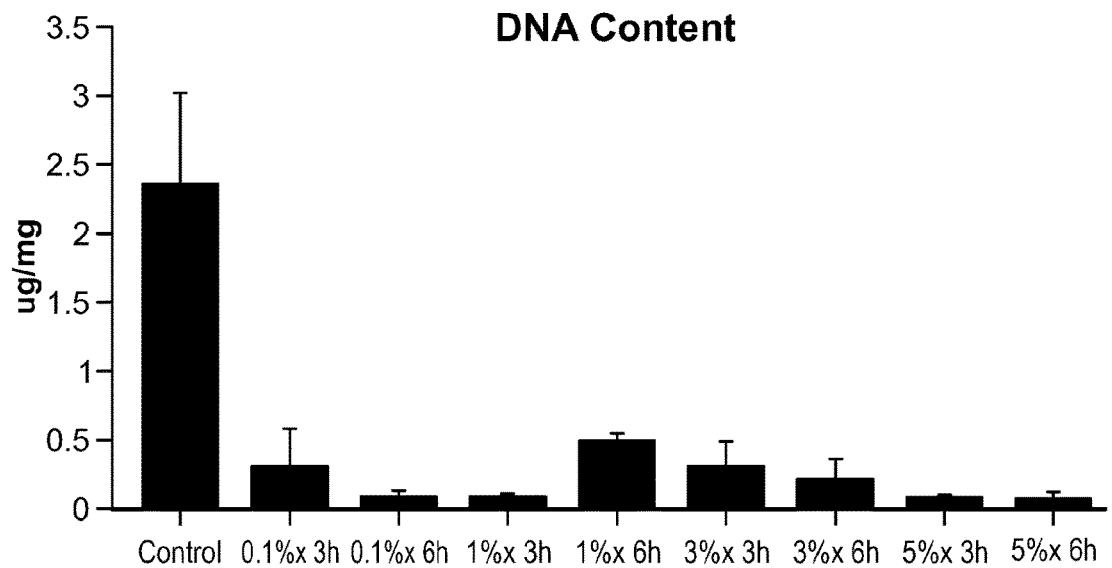
FIG. 4 shows a DNA assay quantifying the remaining DNA content in sample tissues following the various processing methods as compared to un-processed adipose tissue (control).

A rapid emulsion assay was conducted to rule out the presence of residual lipids in the processed tissue. Varying amounts of low levels of lipid were detected in the samples, typically with lower PAA concentrations resulting in more residual lipid remaining in the tissue. An obvious change in the gross and histologic appearance of subcutaneous adipose tissue occurred following processing (FIG. 3). Pre-processed adipose tissue has an orange color reflecting its highly concentrated lipid content (FIG. 3A). Following mechanical disruption and peracetic acid (PAA) exposure, lipid removal correlated with concentration of peracetic acid, as demonstrated by the increasingly white color of the PhAT. Histology with H&E staining also revealed a loss of the lipid laden vacuole cellular architecture of the pre-processed fat (FIG. 3C). Processing of adipose tissue results in condensed ECM with a fibrous appearance consistent with collagen fiber architecture.

Figure 5E:
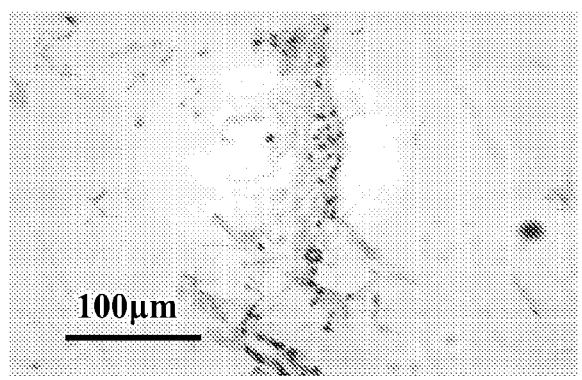

The presence of lipids was also observed histologically. No lipid was observed histologically (FIG. 5E).

Histology:

The scaffolds were fixed overnight in 10% formalin. A series of ethanol (EtOH) solutions were used to dehydrate the samples, which were subsequently embedded in paraffin overnight. Sections were cut to 5 µm thickness, mounted on a microscope slide and allowed to dry for an hour to overnight on a 40° C. plate. Following rehydration, the sections were stained using hematoxylin and eosin (H&E) and Safranin-O/Fast Green. Immunohistochemistry was performed using the Histostain-SP kit (Zymed Laboratories Inc., San Francisco, Calif.) following the manufacturer's protocol. Rabbit polyclonal antibodies to collagen I (Research Diagnostics Inc.) were used as the primary antibodies.

Protein Content:

A comparison of the protein content in the PhAT samples created by the different processing methods was done using a bicinchoninic acid (BCA) protein assay kit (Sigma-Aldrich, B 9643, St. Louis, Mo.) according to the manufacturer's instructions. Briefly, 20 parts of the BCA working reagent are mixed with 1 part of a test sample and incubated at 37° C. for 30 minutes. The absorbance of test samples was read at $\lambda$=562 and compared to standards containing known amounts of albumin. Protein content in samples after treatment with PAA and TX-100 are shown in FIG. 5A.

Figure 9F:
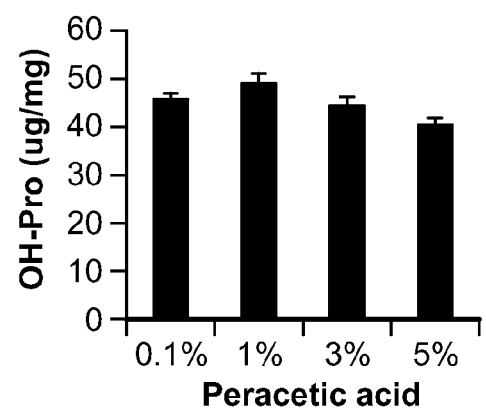
Figure 10A:
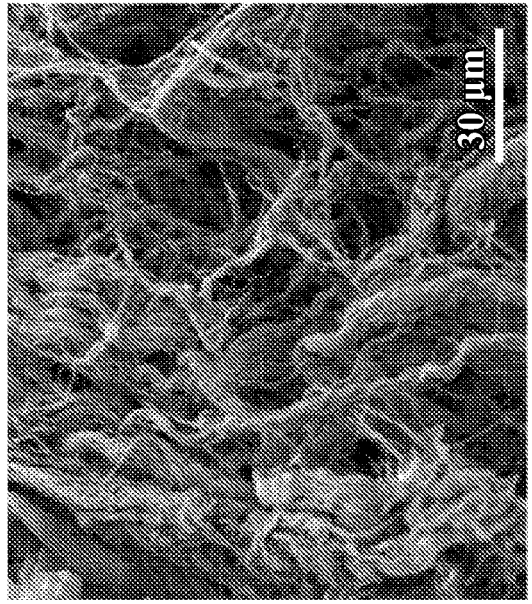
FIGS. 10A-D show scanning electron microscopy images of processed adipose ECM without (top) cells and seeded with cells for 10 days (bottom) at the indicated magnifications. A, B) SEM images, at two magnifications, of the decellularized adipose matrix show the fibrillar collagen structure of the intact ECM with bundles of varying thickness. The ECM is also porous in nature, facilitating cell migration and nutrient diffusion. C, D) SEM images, at two magnifications, of exemplary in vitro experiments with adipose derived stem cells reveal extensive cell adhesion and spreading on the ECM of the decellularized tissue. Multiple cell-ECM contacts can be seen for each cell by day 7 in culture.
Figure 10B:
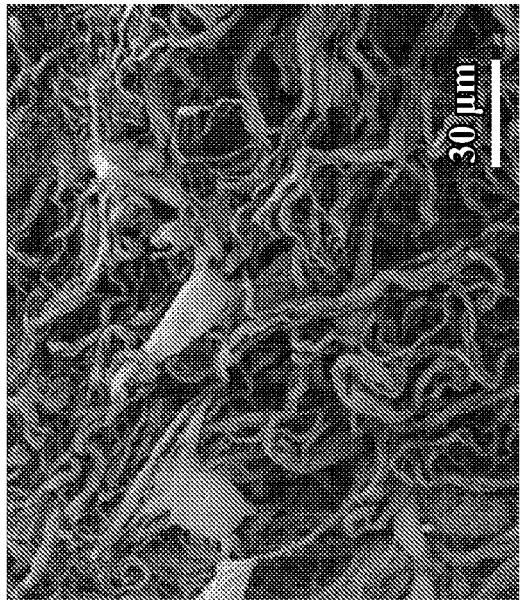
Figure 10C:
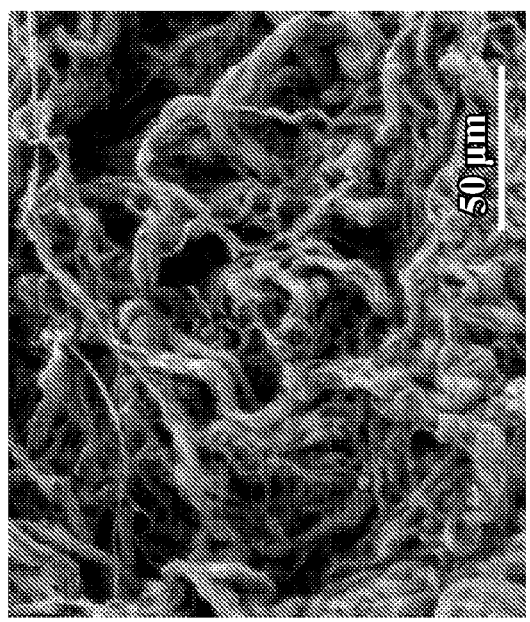
Figure 10D:

Collagen Content:

Briefly, total collagen content was determined by measuring the hydroxyproline concentration of the papain-digests (100 µl) after hydrolysis with 6 N hydrochloric acid at 110° C. overnight and reaction with p-dimethylaminobenzaldehyde and chloramine-T using 0.1 as the ratio of hydroxyproline to total collagen as described previously (Creemers, L. B., et al., Microassay for the assessment of low levels of hydroxyproline. *Biotechniques*. 22:656-658, 1997; Woessner, J. F., Jr. The determination of hydroxyproline in tissue and protein samples containing small proportions of this imino acid. *Arch Biochem Biophys*. 93: 440-4477, 1961, both incorporated herein by reference). A hydroxyproline standard curve was prepared using L-4-hydroxyproline (Fluka, USA). The results are shown in FIGS. 5B and 9F. Again, the specific concentration of PAA had less effect on the amount of collagen remaining in the more finely minced material further treated with TX-100. However, as collagen content began to decrease at higher peracetic acid concentrations, most notably with the 5% peracetic acid (FIG. 9F). At high acid concentrations, the extracellular matrix began to lose its structural integrity and became more difficult to handle. The optimal processing condition was determined by ability to best satisfy the two goals of completely removing cellular material while preserving extracellular matrix structure, ultimately using 3% peracetic acid for subsequent experiments.

ECM Preservation.

Extracellular matrix preservation has been evaluated histologically to assess architecture (H&E and Masson's Trichome stain) (FIGS. 3B, 5C and E, 9D, and 10), quantitatively, using a collagen and proteoglycan biochemical assay, and mechanically. Intact ECM was observed.

Proteoglycan Concentration.

Determination of proteoglycan/glycosaminoglycan concentration was performed on papain digests by the dimethylmethylene blue (DMMB) spectrophotometric assay as previously described. Chondroitin sulfate C (shark cartilage extract, Sigma) was used as the standard (FIG. 5D).

Rheologic Assessment:

Rheological tests were performed on a RFS-3 rheometer (Rheometric Scientific Inc.) using the cone-plate configuration. A 25 mm cone was used with a gap of 0.0584 mm. Pilot dynamic shear strain-sweep test at a frequency of 1 rad/s indicated 0.1% shear strain was in the linear stress-strain range. Dynamic shear strain-sweep tests were performed on all subsequent samples to confirm the linear stress-strain range was similar. The dynamic shear frequency-sweep was tested over a range of frequencies from 0.1 to 100 rad/s at a shear amplitude of 0.1%. The complex modulus at a frequency of 10 was determined to be about $1\times10^3$-$1\times10^5$ Poise.

Dynamic stiffness and compressive moduli of samples were measured using the ELF™ 3200 test instrument. Statistical analysis is performed with the SPSS (version 10.0; SPSS, Chicago, Ill.) software package. Results are shown in FIG. 6. The complex viscosity was shown to decrease with increasing concentrations of PAA.

All biochemical results are presented as means and standard deviations (n=3-4).

Statistical analysis was performed with the SPSS (version 10.0; SPSS, Chicago, Ill.) software package. Statistical significance was determined by ANOVA and post-hoc tests and set as p<0.05.

Example 4—Support of Adipogenicity In Vitro

The processed adipose tissue is assessed for the ability to support cell growth and adipogenesis in vitro. PhAT prepared by the methods of the invention were tested for their ability to support adipogenesis in vitro.

Briefly, samples of the processed materials were seeded with mesenchymal stem cells (MSCs) at a density of $5\times10^3$ or $10\times10^3$ cells per $cm^2$. Adipogenic induction media was added at 24, 48, 72, or 96 hours and percent differentiation was determined at 5, 10, and 15 days by DNA, Oil Red O staining, and Nile red staining. Cells were found to differentiate best when treated with induction media 72-96 hours after seeding and adipogenic differentiation was observed at 5 days.

To further analyze adipogenicity, RNA is extracted from cells seeded on the PAT and RT-PCR for adipose markers including PPAR-γ and Lipo-Protein-Lipase (LPL) is performed and compared to cells expanded in monolayer and those in native adipose tissue as described (Hillel, A., et. al. Embryonic Germ Cells are capable of Adipogenic Differentiation in Vitro and in Vivo. *Tissue Engineering* Part A. 14:1-8, 2008).

Example 5—Scanning Electron Microscopy of PhAT with Cells

Samples were prepared for SEM by fixing in 3.0% formaldehyde/1.5% glutaraldehyde in 0.1M sodium cacodylate buffer solution with 2.5% sucrose for 1 hour at room temperature. Samples were then post-fixed with 1% osmium tetroxide for 30 minutes shielded from light at room temperature before dehydration with graded ethanol solutions. $CO_2$ critical point drying was carried out, followed by sputter-coating with platinum and images were taken on a FEI Quanta 200 SEM (Hillsboro, Oreg.).

SEM images of the decellularized adipose matrix show the fibrillar collagen structure of the ECM with bundles of varying thickness (FIG. 10 A, B). The ECM is also porous in nature, facilitating cell migration and nutrient diffusion. In vitro experiments with adipose derived stem cells reveal extensive cell adhesion and spreading on the ECM of the decellularized tissue (FIG. 10 C, D). Multiple cell-ECM contacts can be seen for each cell by day 7 in culture.

Example 6—Crosslinking of PhAT and Resistance to Degradation In Vitro

PhAT prepared using PAA/DNAse I/TX-100 treatments was crosslinked using N-(3-dimethylaminopropyl)-N-ethylcarbodiimide (EDC) and N-hydroxysuccinimide (NHS) in 50 mM 2-(N-morpholino)ethanesulfonic acid (MES) buffer at pH 5.5. Samples were incubated with crosslinking solutions for 4 hours at concentrations of 5, 10, 50, and 100 mM EDC with an EDC:NHS molar ratio of 2:1. Residual crosslinkers were removed by rinsing with 0.1 M $Na_2HPO_4$ for 2 hours followed by four additional 30 minute incubations with distilled water.

EDC crosslinking was compared with a different chemical crosslinker, hexamethylene diisocyanate (HMDC). Due to its instability in aqueous solutions, previous studies from which we based our methods have used secondary alcohols as the solvent or used surfactants to preserve HMDC reactivity. For the secondary alcohol suspension, 1% and 5% HMDC solutions were made in 2-propanol. Samples were dehydrated in 2-propanol for 2 changes at 30 minutes each, prior to incubation for 4 hours in the crosslinking solution. Samples were rinsed with 100% 2-propanol twice for 30 minutes each, followed by rehydration using graded 2-propanol solutions and 4 additional rinses with distilled water for 30 minutes each.

Samples were also crosslinked with 1% and 5% HMDC in a surfactant solution containing 1% Tween 20 in a phosphate buffer (0.054 M $Na_2HPO_3$, 0.013 M $NaH_2PO_4$) at pH 7.4. Crosslinking was carried out at room temperature for 4 hours, followed by extensive rinses with distilled water, two 30 minute incubations with 4 M NaCl, and four additional rinses with distilled water for 30 minutes each to remove the surfactant and residual crosslinkers.

The different crosslinking conditions were characterized by comparing their susceptibility to enzymatic degradation. Crosslinked samples and uncrosslinked controls were lyophilized for two days to reduce variability based on water content. The samples were then incubated with 200 U/ml collagenase I in 0.05 M Tris-HCl (pH 7.5) in an incubator at 37° C. At timepoints of 1, 3, 8, 16, and 24 hours, the samples were spun down and supernatants collected and stored at −20° C. until completion of the experiment. Fresh collagenase was added and samples were returned to the incubator until the next designated timepoint. After collecting the supernatant at 24 hours, any remaining extracellular matrix was digested with a 125 μg/ml papainase solution for 16 hours in a 60° C. water bath. Finally, all the supernatants and papain digested samples were analyzed using the aforementioned collagen assay to determine the amount of collagen solubilized to obtain the percentage of total collagen degraded at the different timepoints. Three samples for each crosslinking condition were used.

Figure 11A:
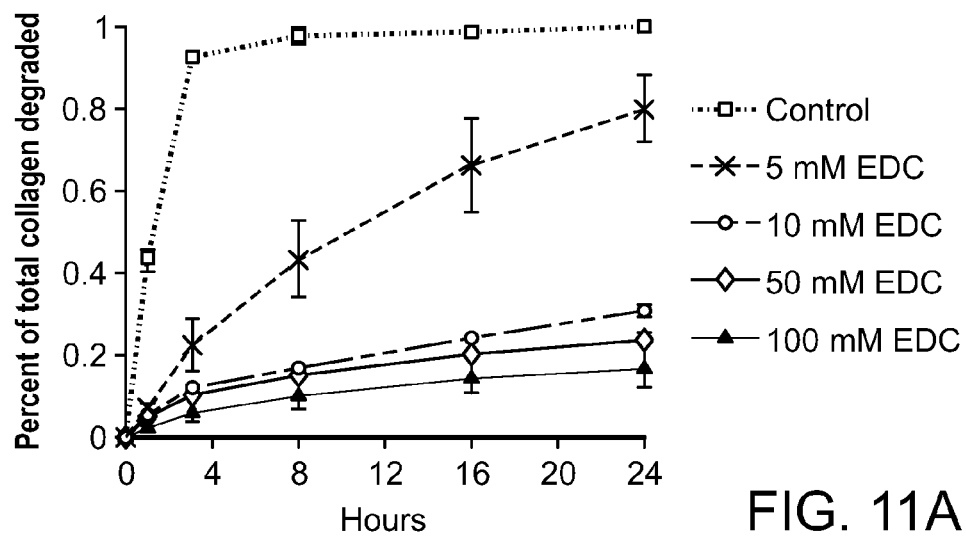
FIGS. 11A-C show resistance of non-crosslinked and crosslinked PhAT to enzymatic degradation as determined by the percent of total collagen degraded over 24 hours when incubated with collagenase for uncrosslinked control tissue and crosslinked ECM. A) shows PhAT (adipose ECM) crosslinked with 5-100 mM EDC. B) shows PhAT crosslinked with 1% and 5% HMDC in Tween® 20. C) shows PhAT crosslinked with 1% and 5% HMDC in 2-propanol (100%).
Figure 11B:
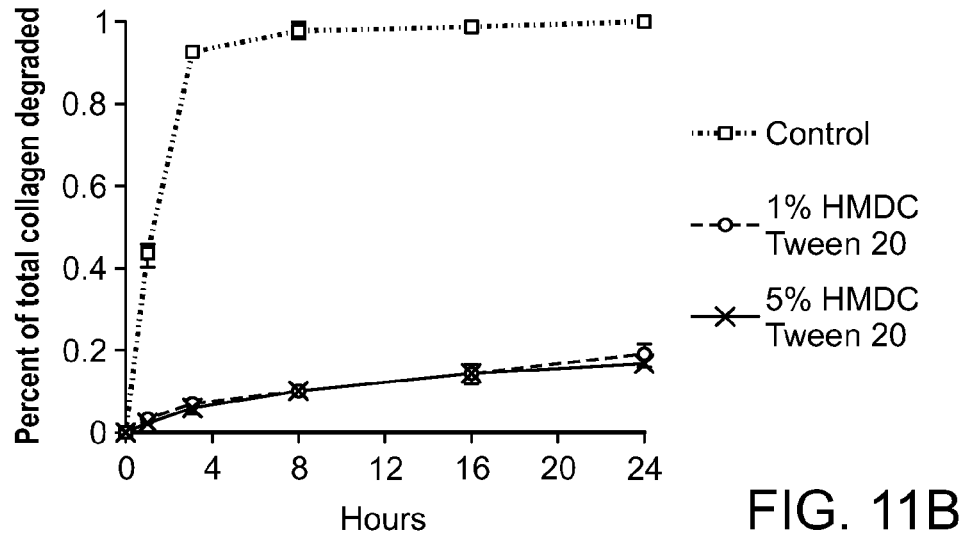
Figure 11C:
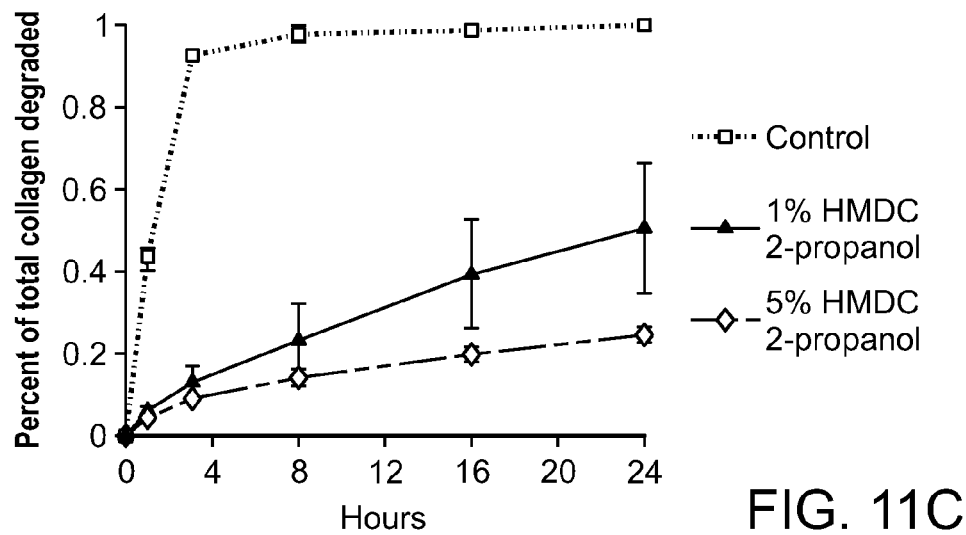

EDC-crosslinked samples showed greater resistance to enzymatic degradation in comparison to uncrosslinked controls when incubated with collagenase (FIG. 11A). Resistance to degradation increased with higher concentrations of the chemical crosslinker. HMDC crosslinking resulted in different degradation properties depending on the solvent used. When suspended in a 1% Tween 20 solution, very little degradation occurred with no differences observed between 1% or 5% HMDC concentrations (FIG. 11B). When HMDC was suspended in 2-propanol, crosslinked samples in 1% HMDC were more susceptible to collagenase degradation than those in 5% HMDC (FIG. 11C).

Example 7—Support of Cell Viability In Vitro

Live/Dead assay (Molecular Probes) were performed to demonstrate that the PhAT prepared by any of the methods provided herein were found to support cell viability.

With an 8 mm punch biopsy, scaffolds were made from each PhAT treated with various concentrations of PAA and with DNAse, lyophilized to facilitate cell seeding, and reconstituted with human mesenchymal stem cells (MSCs) at a concentration of 50,000 cells/30 ul of DMEM. Scaffolds were cultured in adipogenic media (DMEM supplemented with FBS and 0.5 mM of dexamethasone (Sigma; St. Louis, Mo.), 1 mg/mL insulin (Sigma; St. Louis, Mo.), and 0.5 mM 1-methyl-3-isobutylmethyl-xanthene (IBMX; (Sigma; St. Louis, Mo.)) at 5% $CO_2$ at 37° C. After 24 hours and 1 week of culture, sections of the various PhAT scaffolds were cut and incubated in live/dead solution for 30 minutes (live/dead solution; calcein AM:EthD-homodimer1:DMEM (0.5:4: 2000)). After 30 minutes of incubation, sections were washed and cell viability was observed under a fluorescent microscope as described by the manufacturer (Molecular Probes). Following cell seeding, Live/Dead assay performed at day 1 and day 7. In every case, live cells were present after 24 hours of culturing on the processed adipose tissue. Greater cell viability was found for 3% PAA (3 and 6 hours) PhAT with decreasing viability in 5% PAA×3 hours, and almost minimal viability with 5% PAA×6 hours. By day 7 live cells outnumber dead cells (red nuclear staining) only in PAT processed with 3% PAA.

Cross-linked PhAT preparations were also tested for the ability to support cell viability using a similar method. Chemical crosslinkers can be cytotoxic if residual crosslinkers are left in the tissue and the solvents used can also be detrimental to cell survival if incompletely removed. PhAT was prepared by forcing the adipose tissue through a die, and sequential treatment with 3% PAA, TX-100, and DNAse I as described above. Samples were then cross-linked as described below using 5-100 mM EDC, 1-5% HMDC in the presence of 1% Tween® 20, 1-5% HMDC in 2-propanol (100%). Cells were seeded at 40,000 cells per scaffold in a 48 well plate and cultured for 5 days in ASC maintenance media (DMEM-F12, 10% FBS, 100 U/ml penicillin, 10 µg/ml streptomycin).

Cell viability was assessed using a LIVE/DEAD Viability/Cytotoxicity Kit (Invitrogen, Carlsbad, Calif.). Cell-ECM scaffolds were incubated in live/dead media containing 4 µM calcein AM and 4 µM ethidium homodimer-1 in DMEM-F12 for 30 minutes at 37° C. and 5% $CO_2$. Upon completion of incubation, live/dead medium was removed from wells and scaffolds rinsed with PBS. Cytotoxicity was assessed using fluorescence microscopy with 485±10 nm and 530±12.5 nm optical filters to visualize live and dead cells, respectively.

Cells were viable and proliferating even in the conditions of highest crosslinker concentrations at both 1 and 5 days with far more live cells than dead after five days in culture for each of the conditions, compared to uncrosslinked controls. The condition that was least conducive to cell growth appeared to be HMDC in 2-propanol and was therefore excluded in the subsequent in vivo study.

Example 8—Assessment In Vivo of Processed Adipose Tissue

Figure 7A:
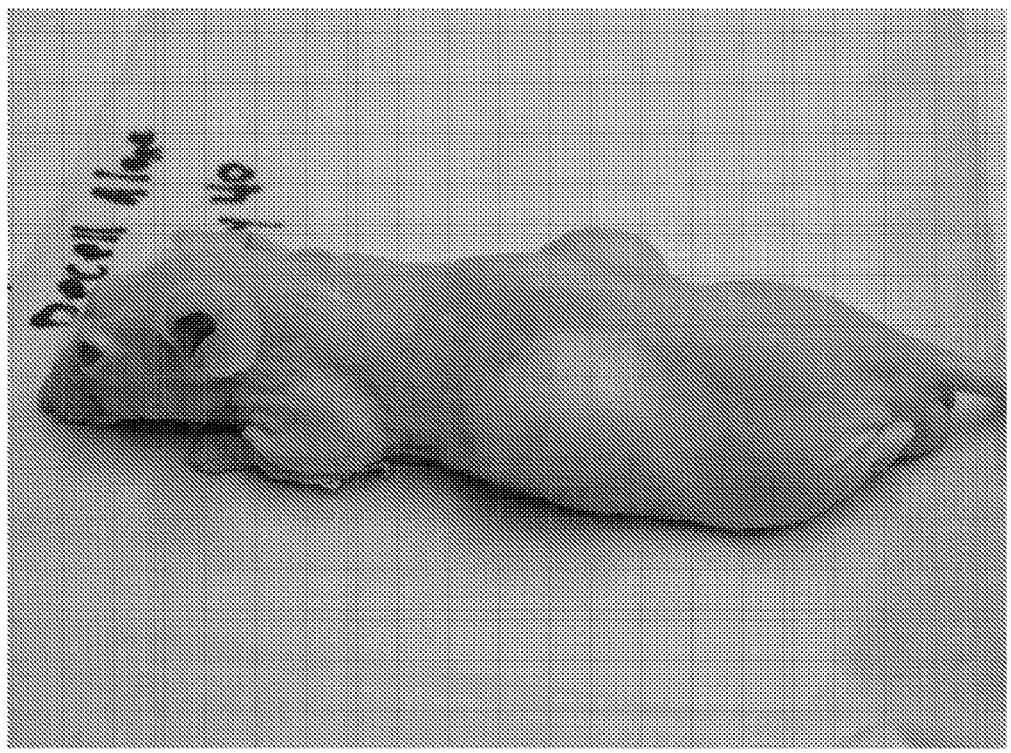
FIGS. 7A-D show A-B) gross images of implanted processed adipose tissue in an athymic mouse 40 days after implantation; C) Implanted processed adipose tissue in a rat at day 45; and D) 4×H&E stain of processed adipose tissue following implantation in a rat at day 45.
Figure 7B:
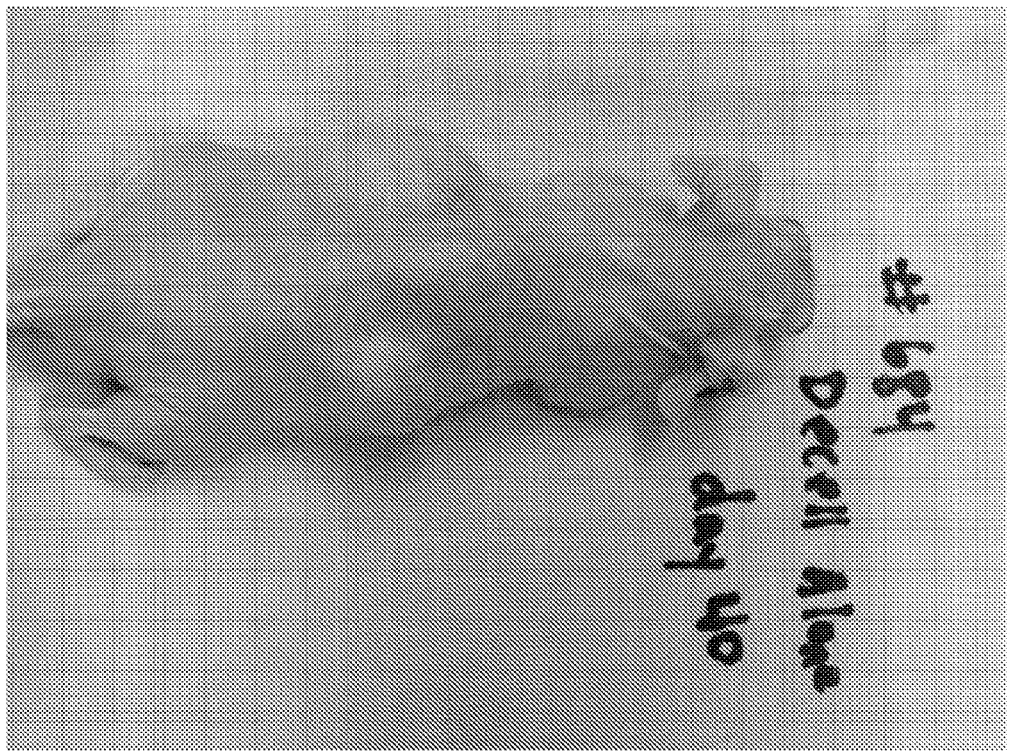
Figure 7C:
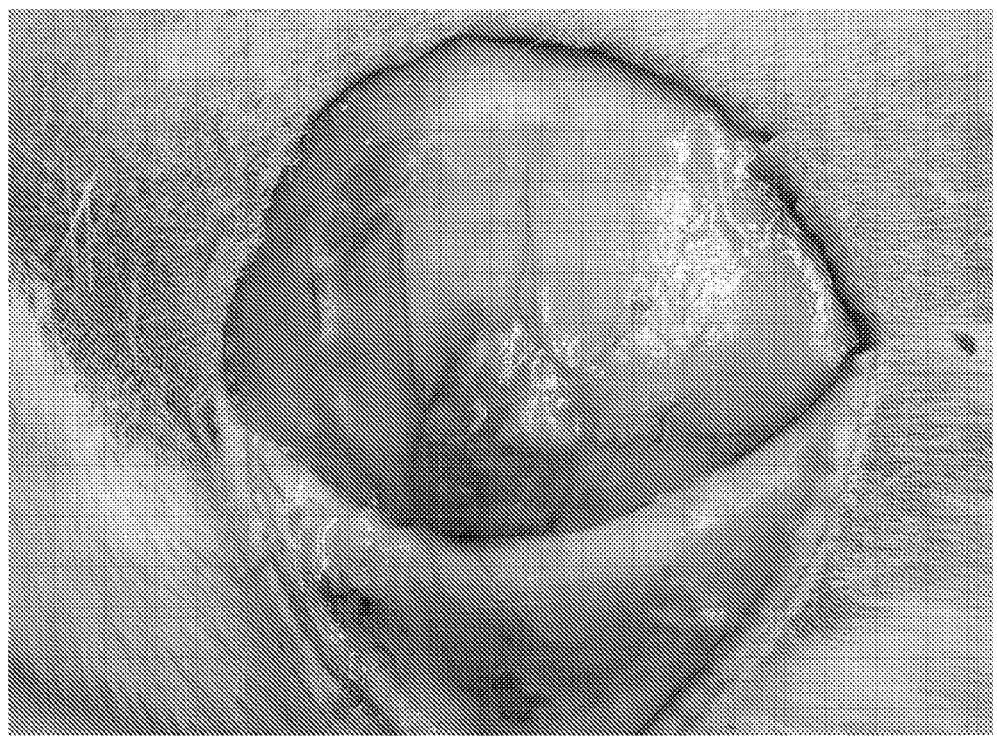
Figure 7D:
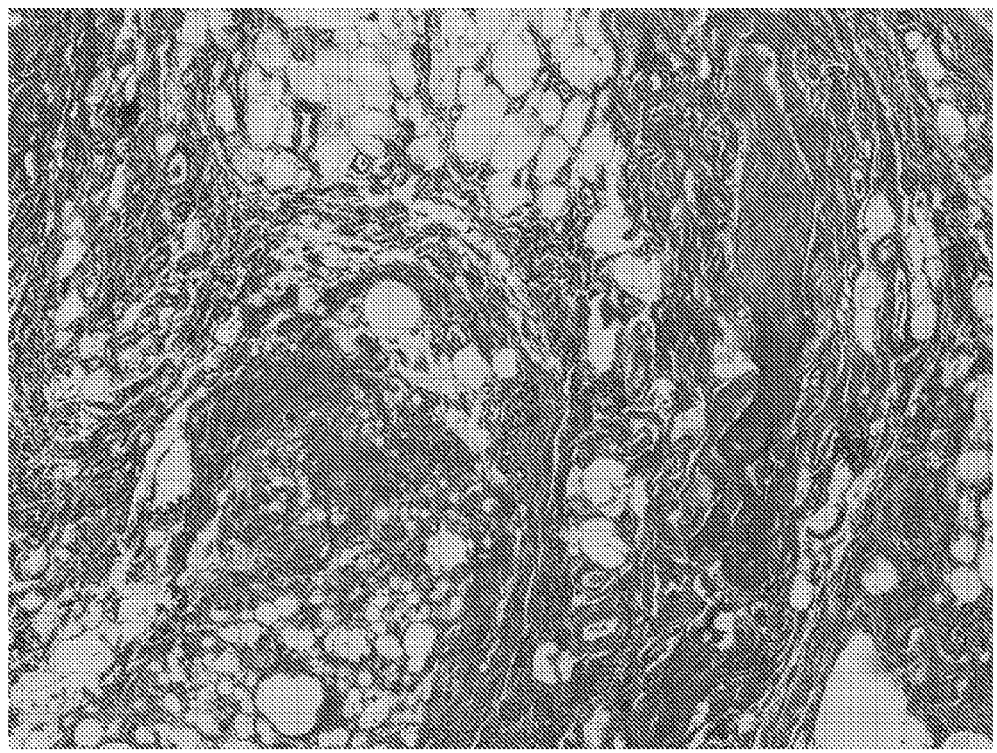

One milliliter of PhAT prepared by treatment with PAA and DNAse I was implanted subcutaneously on the dorsum of a Sprague-Dawley rat and 500 ul on an athymic nude mouse. Photographs of representative mice 40 days after implantation of the PhAT are shown in FIGS. 7A and B. The implants were monitored over time via palpation and measurements were taken using a caliper and found to persist at 45 days from the time of implantation. The PhAT was palpable throughout the experiment and visible upon removal of the skin over the PhAT (FIG. 7C). At day 45, the animals were sacrificed and the material was harvested for histology. Histology demonstrated evidence of integration with surrounding tissue, angiogenesis, and minimal inflammation (FIG. 7D).

Example 9—In Vivo Persistence and Biocompatibility Studies

Persistence and biocompatibility of preferred matrices were tested in vivo with subcutaneous implantation in rats. All procedures were performed with prior approval from the Johns Hopkins Animal Care and Use Committee. PhAT was implanted subcutaneously on the dorsum of eight-week-old female Sprague-Dawley rats (n=4). To measure persistence, the length, width, and depth of each implant site was measured using a digital caliper and recorded three times and averaged. Assuming an ellipsoid shape for the implant, the equation $(4/3)(\pi)(\frac{1}{2}\text{ height})(\frac{1}{2}\text{ length})(\frac{1}{2}\text{ width})$ was used to calculate the volume using the average of each dimension. These measurements were done immediately after injection, at 1 and 3 weeks. The volume was then plotted over time and the results are shown in FIGS. 8A and B. Following euthanasia at 1 and 3 weeks, the implants were extracted and fixed in 10% formalin overnight and stained using H&E. Histologic evaluation of the inflammatory response to PhAT implantation, cellular influx and vascularization of PhAT was used to assess biocompatibility.

There was evidence of cellular influx into the tissue, most likely consisting of fibroblasts given their fibroblastic morphology. Full lumen vessels were identified infrequently.

Caliper measurements indicated an initial decrease in the absolute height and volume ratio at 1 week, which appears to level off by 3 weeks (FIG. 8A-B). The histological appearance of the tissue at harvest time demonstrates far greater tissue density than its appearance pre-implant, indicating that though some initial degradation may account for the decrease in the volume of the implant over time, tissue compaction underneath the muscular skin of a rat may also be contributing to the initial decrease in volume.

Biocompatibility studies were also performed using crosslinked PhAT. After two weeks of implantation, adipose ECM implants were opaque and vascularization could be observed at the surface (FIG. 12). Inflammatory cells were present predominantly at the periphery of the implant.

Figure 13:
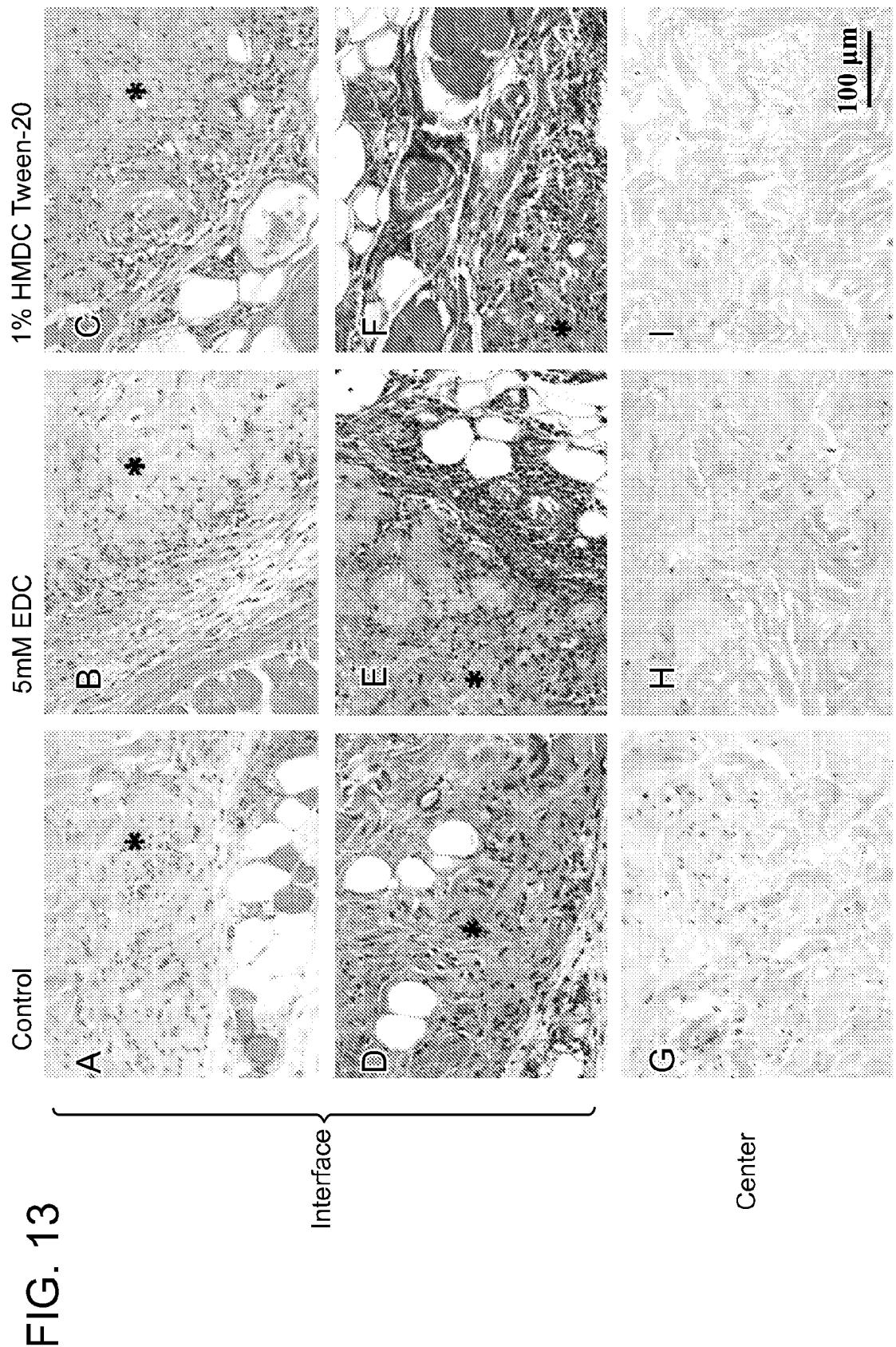
FIGS. 13A-I show the histology of subcutaneous implants after two weeks at the (A-F) interface and (G-I) center of the implant. Implanted extracellular matrix is denoted by an asterisk for images taken at the interface for (A, D, G) control, (B, E, H) 5 mM EDC crosslinked, and (C, F, I) 1% HMDC Tween®-20 crosslinked tissue.

Although there was not an extensive inflammatory reaction, the most prominent fibrous capsule formed with the 5 mM EDC crosslinked ECM. Cell migration into the implant reflected the presence of a fibrous capsule, with fewer cells migrating to the center in the crosslinked scaffolds compared to controls (FIG. 13). From this data, it can be concluded that ECM can be crosslinked and implanted in vivo without eliciting a severe immune response, thereby providing a mechanism to modulate degradation profiles and mechanical properties of the biomaterial.

In a second study using the crosslinked PhAT was evaluated by in vivo injection studies in rats with prior approval from the Johns Hopkins Animal Care and Use Committee. 12-week-old Sprague-Dawley rats (n=2) were injected subcutaneously with 400 µL of decellularized adipose extracellular matrix of the following conditions: uncrosslinked (control), 5 mM EDC-crosslinked, or 1% HMDC-crosslinked in Tween 20, with two injections of each condition in the dorsum. Implants were removed after 3 weeks and fixed with 10% formalin for histological analysis. Specimens were dehydrated through a series of graded ethanol solutions and cleared in xylene before embedding in paraffin. The implants were sectioned at 5 µm thickness, rehydrated, and subsequently stained with hematoxylin and eosin as well as Masson's trichrome to evaluate implant biocompatibility. Monitoring implant persistence showed maintenance of a stable implant volume after the first week of implantation. Good integration with host tissue and cell infiltration could be observed in the center of the implant, suggesting that with significant migration of cells and subsequent remodeling of the ECM, tissue regeneration could maintain a volume-stable implant.

Example 10—Dynamic Rheologic Property Assessment of Processed Adipose Tissue at 0.63 Rad/Sec Rheologic properties of the processed adipose tissue were assayed using known methods such as those described above (see also, e.g., Falcone and Berg, 2009. Temporary polysaccharide dermal fillers: A model for persistence based on physical properties. *Dermatol. Surg.* 35:1-6, incorporated herein by reference). The results are provided in the table below:

TABLE 1

Dynamic Rheologic Properties of PhAT at 0.63 rad/s

| Material | η* (Pas) | G* (Pa) | G' (Pa) | G" (Pa) | Tan (δ) |
|---|---|---|---|---|---|
| Fat | $2.5 \times 10^5$ | $1.6 \times 10^5$ | $1.58 \times 10^5$ | $2.3 \times 10^4$ | .1455 |
| 3% PAA × 3 h | $8.2 \times 10^4$ | $5.2 \times 10^4$ | $5.1 \times 10^4$ | $8.8 \times 10^3$ | .17175 |
| 3% PAA × 6 h | $2.5 \times 10^4$ | $1.6 \times 10^4$ | $1.5 \times 10^4$ | $2.6 \times 10^3$ | .16917 |
| 5% PAA × 3 h | $3.6 \times 10^4$ | $2.2 \times 10^4$ | $2.2 \times 10^4$ | $3.6 \times 10^3$ | .16208 |
| 5% PAA × 6 h | $1.4 \times 10^4$ | $8.7 \times 10^3$ | $8.6 \times 10^3$ | $1.0 \times 10^3$ | .12074 |

η* (Pas): Complex Viscosity, measured in Poise
G* (Pa): Complex Modulus, measured in Pascal
G' (Pa): Elastic Modulus, measured in Pascal
G" (Pa): Viscous Modulus, measured in Pascal
Tan (δ): Tangent delta
^ indicates superscript Those skilled in the art will recognize, or be able to ascertain using no more than routine experimentation, many equivalents to the specific embodiments of the invention described herein. Such equivalents are intended to be encompassed by the following claims.

All references, patents, and patent publications cited herein are incorporated herein by reference as if they were each incorporated individually.

1. Kaufman, M. R., Bradley, J., Dickenson, B., et al., Autologous Fat Transfer National Consensus Survey: Trends in Techniques for Harvest, Preparation, and Application, and Perception of Short- and Long-Term Results. Plastic and Reconstructive Surgery. Volume 119(1), January 2007, pp 323-331.
2. Butterwick, K. J., Nootheti, P. K., Hsu, J. W., et al., Autologous Fat Transfer: An In-Depth Look at Varying Concepts and Techniques. Facial Plastics Surgery Clinics of North America. Volume 15, 2007, pp 99-111.
3. Uriel, S., Huang, J., Moya, M. L., et al., The Role of Adipose Derived Protein Hydrogels in Adipogenesis. Biomaterials. Volume 29, 2008, pp 3712-3719.
4. Creemers, L. B., et al., Microassay for the assessment of low levels of hydroxyproline. Biotechniques. Volume 22(4), 1997, pp 656-658.
5. Woessner, J. F., Jr., The determination of hydroxyproline in tissue and protein samples containing small proportions of this imino acid. Arch Biochem Biophys. Volume 93, 1961, pp 440-4477.
6. Liang, H.-C., et al., The effects of crosslinking degree of an acellular biological tissue on its tissue regeneration pattern. Biomaterials. 25:3541-3552, 2004.
7. Kelly J L, Findlay M W, Knight K R, Penington A, Thompson E W, Messina A, Morrison W A. Contact with existing adipose tissue is inductive for adipogenesis in matrigel. Tissue Eng. 2006 July; 12(7):2041-7.
8. Stillaert F, Findlay M, Palmer J, Idrizi R, Cheang S, Messina A, Abberton K, Morrison W, Thompson E W. Host rather than graft origin of Matrigel-induced adipose tissue in the murine tissue-engineering chamber. Tissue Eng. 2007 September; 13(9):2291-300.
9. Aditya Chaubey and Karen J. L. Extracellular Matrix Components as Modulators of Adult Stem Cell Differentiation in an Adipose System. Journal of Bioactive and Compatible Polymers. Burg 2008; 23; 20

We claim:

1. An acellular delipidized biocompatible biomaterial comprising a mammalian adipose tissue extracellular matrix (ECM) derived from cadaveric adipose tissue, the biomaterial having between 1% to 0.001% adipose lipid by weight and a complex viscosity of $1 \times 10^4$ to $9 \times 10^5$ Pas, wherein the biomaterial is non-inflammatory when implanted.

2. The biomaterial of claim 1, wherein the complex viscosity is $1 \times 10^4$ to $8 \times 10^5$ Pas.

3. The biomaterial of claim 1, wherein the complex viscosity is $1 \times 10^4$ to $3 \times 10^5$ Pas.

4. The biomaterial of claim 1, further comprising a cross-linking agent.

5. The biomaterial of claim 4, wherein the cross-linking agent is selected from the group consisting of carbodiimide (EDC), hexamethylene diisocyanate (HMDC), gluteraldehyde, proanthocyanidin, ribose, threose, and lysyl oxidase, carbodiimide, polyepoxy ethers, divinyl sulfone (DVS), genipin, polyaldehyde and diphenylphosphoryl azide (DPPA), genipin, epoxy compounds, dialdehyde starch, glutaraldehyde, formaldehyde, dimethyl suberimidate, carbodiimides, succinimidyls, diisocyanates, and acyl azide.

6. The biomaterial of claim 1, wherein the biomaterial is injectable.

7. The biomaterial of claim 1, wherein the biomaterial is sterilized.

8. An acellular delipidized biocompatible biomaterial comprising a mammalian adipose tissue extracellular matrix (ECM) derived from cadaveric adipose tissue, the biomaterial having between 1% to 0.001% adipose lipid by weight and a complex modulus of $5 \times 10^3$ to $1 \times 10^5$ Pa, wherein the biomaterial is non-inflammatory when implanted.

9. The biomaterial of claim 8, wherein the complex modulus is $1 \times 10^4$ to $1 \times 10^5$ Pa.

10. The biomaterial of claim 8, wherein the complex modulus is $1 \times 10^4$ to $9 \times 10^4$ Pa.

11. The biomaterial of claim 8, further comprising a cross-linking agent.

12. The biomaterial of claim 11, wherein the cross-linking agent is selected from the group consisting of carbodiimide (EDC), hexamethylene diisocyanate (HMDC), gluteraldehyde, proanthocyanidin, ribose, threose, and lysyl oxidase, carbodiimide, polyepoxy ethers, divinyl sulfone (DVS), genipin, polyaldehyde and diphenylphosphoryl azide (DPPA), genipin, epoxy compounds, dialdehyde starch, glutaraldehyde, formaldehyde, dimethyl suberimidate, carbodiimides, succinimidyls, diisocyanates, and acyl azide.

13. The biomaterial of claim 8, wherein the biomaterial is injectable.

14. An acellular delipidized biocompatible biomaterial comprising a mammalian adipose tissue extracellular matrix (ECM) derived from cadaveric adipose tissue, the biomaterial having between 1% to 0.001% adipose lipid by weight and an elastic modulus of $5 \times 10^3$ to $1 \times 10^5$ Pa, wherein the biomaterial is non-inflammatory when implanted.

15. The biomaterial of claim 14, wherein the elastic modulus is $1 \times 10^4$ to $1 \times 10^5$ Pa.

16. The biomaterial of claim 14, wherein the elastic modulus is $1 \times 10^4$ to $9 \times 10^4$ Pa.

17. The biomaterial of claim 14, further comprising a cross-linking agent.

18. The biomaterial of claim 17, wherein the cross-linking agent is selected from the group consisting of carbodiimide (EDC), hexamethylene diisocyanate (HMDC), gluteraldehyde, proanthocyanidin, ribose, threose, and lysyl oxidase, carbodiimide, polyepoxy ethers, divinyl sulfone (DVS), genipin, polyaldehyde and diphenylphosphoryl azide (DPPA), genipin, epoxy compounds, dialdehyde starch, glutaraldehyde, formaldehyde, dimethyl suberimidate, carbodiimides, succinimidyls, diisocyanates, and acyl azide.

19. The biomaterial of claim 14, wherein the biomaterial is injectable.

20. An acellular delipidized biocompatible biomaterial comprising a mammalian adipose tissue extracellular matrix (ECM) derived from cadaveric adipose tissue, the biomaterial having between 1% to 0.001% adipose lipid by weight and a viscous modulus of $5 \times 10^3$ to $1 \times 10^5$ Pa, wherein the biomaterial is non-inflammatory when implanted.

21. The biomaterial of claim 20, wherein the viscous modulus is $1 \times 10^4$ to $1 \times 10^5$ Pa.

22. The biomaterial of claim 20, wherein the viscous modulus is $1 \times 10^4$ to $9 \times 10^4$ Pa.

23. The biomaterial of claim 20, further comprising a cross-linking agent.

24. The biomaterial of claim 23, wherein the cross-linking agent is selected from the group consisting of carbodiimide (EDC), hexamethylene diisocyanate (HMDC), gluteraldehyde, proanthocyanidin, ribose, threose, and lysyl oxidase, carbodiimide, polyepoxy ethers, divinyl sulfone (DVS), genipin, polyaldehyde and diphenylphosphoryl azide (DPPA), genipin, epoxy compounds, dialdehyde starch, glutaraldehyde, formaldehyde, dimethyl suberimidate, carbodiimides, succinimidyls, diisocyanates, and acyl azide.

25. The biomaterial of claim 20, wherein the biomaterial is injectable.

26. An acellular delipidized biocompatible biomaterial comprising a mammalian adipose tissue extracellular matrix (ECM) derived from cadaveric adipose tissue, the biomaterial having between 1% to 0.001% adipose lipid by weight and a tan (δ) of 0.05 to 2.0, wherein the biomaterial is non-inflammatory when implanted.

27. The biomaterial of claim 26, wherein the tan (δ) is 0.1 to 1.0.

28. The biomaterial of claim 26, wherein the tan (δ) of 0.1 to 0.75.

29. The biomaterial of claim 26, further comprising a cross-linking agent.

30. The biomaterial of claim 29, wherein the cross-linking agent is selected from the group consisting of carbodiimide (EDC), hexamethylene diisocyanate (HMDC), gluteraldehyde, proanthocyanidin, ribose, threose, and lysyl oxidase, carbodiimide, polyepoxy ethers, divinyl sulfone (DVS), genipin, polyaldehyde and diphenylphosphoryl azide (DPPA), genipin, epoxy compounds, dialdehyde starch, glutaraldehyde, formaldehyde, dimethyl suberimidate, carbodiimides, succinimidyls, diisocyanates, and acyl azide.

31. The biomaterial of claim 26, wherein the biomaterial is injectable.

32. A composition comprising at least one biomaterial of claim 1 and at least one pharmaceutically acceptable carrier or adjuvant.

33. A composition comprising at least one biomaterial of claim 8 and at least one pharmaceutically acceptable carrier or adjuvant.

34. A composition comprising at least one biomaterial of claim 14 and at least one pharmaceutically acceptable carrier or adjuvant.

35. A composition comprising at least one biomaterial of claim 20 and at least one pharmaceutically acceptable carrier or adjuvant.

36. A composition comprising at least one biomaterial of claim 26 and at least one pharmaceutically acceptable carrier or adjuvant.

* * * * *